United States Patent
Fontana et al.

(10) Patent No.: US 7,498,452 B2
(45) Date of Patent: Mar. 3, 2009

(54) TAXANE DERIVATIVES FUNCTIONALIZED AT THE 14-POSITION AND A PROCESS FOR THE PREPARATION THEREOF

(75) Inventors: Gabriele Fontana, Milan (IT); Ezio Bombardelli, Milan (IT); Arturo Battaglia, Bologna (IT); Eleonora Baldelli, Bologna (IT); Andrea Guerrini, Bologna (IT); Maria Luisa Gelmi, Milan (IT); Giacomo Carenzi, Busto Arsizio (IT); Donato Pocar, Milan (IT)

(73) Assignee: Indena S.p.A., Milan (IT)

( * ) Notice: Subject to any disclaimer, the term of this patent is extended or adjusted under 35 U.S.C. 154(b) by 84 days.

(21) Appl. No.: 10/527,164

(22) PCT Filed: Sep. 5, 2003

(86) PCT No.: PCT/EP03/09866

§ 371 (c)(1),
(2), (4) Date: Nov. 9, 2005

(87) PCT Pub. No.: WO2004/024706

PCT Pub. Date: Mar. 25, 2004

(65) Prior Publication Data

US 2006/0122258 A1  Jun. 8, 2006

(30) Foreign Application Priority Data

Sep. 10, 2002  (IT) .......................... MI2002A1921

(51) Int. Cl.
    *C07D 31/21* (2006.01)
(52) U.S. Cl. ....................... 549/510; 549/511
(58) Field of Classification Search ................. 549/510, 549/511
    See application file for complete search history.

(56) References Cited

U.S. PATENT DOCUMENTS 5,705,508 A  *  1/1998  Ojima et al. ................. 514/320
5,821,363 A      10/1998  Kelly et al.

FOREIGN PATENT DOCUMENTS

| WO | WO 94/22856 | 10/1994 |
|----|-------------|---------|
| WO | WO 02/12215 | 2/2002  |

* cited by examiner

*Primary Examiner*—Janet L. Andres
*Assistant Examiner*—Raymond Covington
(74) *Attorney, Agent, or Firm*—Young & Thompson

(57) ABSTRACT

A general process for the functionalization at the 14-position of 13-ketobaccatin derivatives of formula I to give derivatives of formula II wherein the substituents are as defined in the disclosure. The conversion of compounds of formula II in compounds of formula III, wherein the substituents are as defined in the disclosure, is also described.

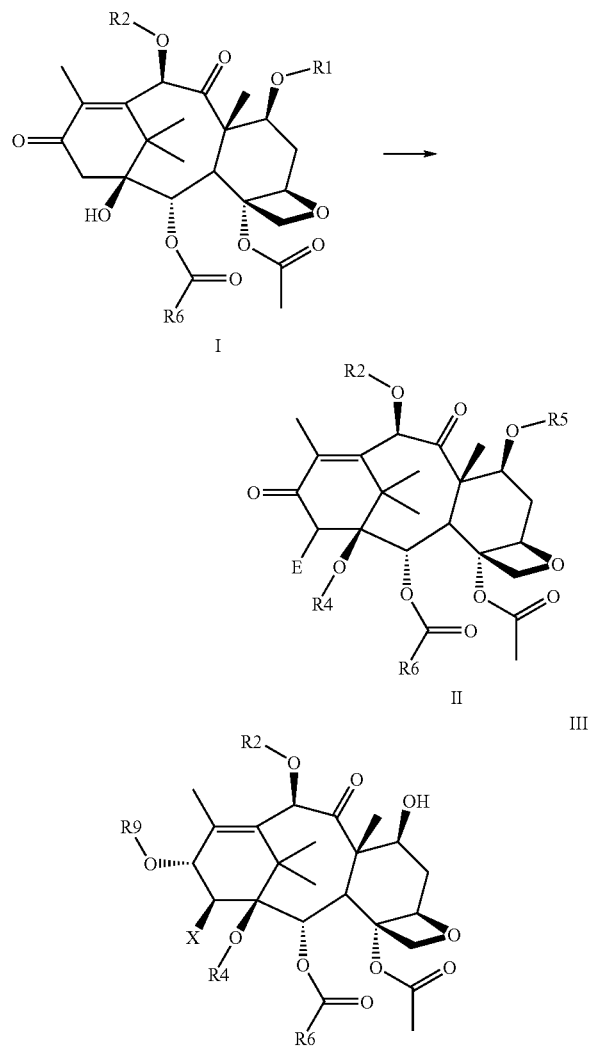

8 Claims, No Drawings

TAXANE DERIVATIVES FUNCTIONALIZED AT THE 14-POSITION AND A PROCESS FOR THE PREPARATION THEREOF

DISCLOSURE

The present invention relates to novel 13-ketobaccatin III and taxane derivatives and to the processes for the preparation thereof.

TECHNOLOGICAL BACKGROUND

WO 94/22856 discloses 14-hydroxy-taxanes having improved antitumor properties compared with conventional taxanes. One of said 14-hydroxy derivatives, referred to as IDN 5109, is at present under advanced clinical development. Said 14-hydroxylated derivatives can be easily prepared from natural 14-hydroxybaccatin.

It has now been found that IDN 5109 analogues bearing different substituents than the hydroxy group at the 14-position have surprising biological activity, as they are effective not only against taxane-resistant tumors but also against MDR cell lines.

The derivatives of the invention can be obtained by enolization of 13-ketobaccatin III and treatment with suitable electrophiles which can be converted into the desired group. Subsequent reduction of the C13 carbonyl and esterification with isoserine chains afford the compounds of the invention, as defined below.

7-Protected 13-ketobaccatin III is a very interesting compound as a key intermediate to 12,13-isotaxanes (Wicnienski et al., U.S. Pat. No. 5,821,363), to novel taxanes modified at the 13-position (Menichincheri et al., WO9614308) and at the C and D ring (Dubois et al., Tetrahedr. Lett. 2000, 41, 3331-3334; Uoto et al., Chem. Pharm. Bull. 1997, 45(12), 2093-2095). 7-Protected 13-ketobaccatin III is an important intermediate in the studies on total synthesis of taxol and analogues (Nicolaou et al., J. Am. Chem. Soc. 1995, 117, 624-633; Nicolaou et al. 1995, 117, 2409-2420; Nicolaou et al., U.S. Pat. No. 5,504,222). Some modifications of 7-protected 13-ketobaccatin III have also been reported, such as formation of hydrazones and oximes, (Menichincheri et al., WO9614308; Meninchincheri et al., Med. Chem. Res. (1996), 6(4), 264-292), direct treatment with oxidizing agents (Bombardelli et al., WO0212215; Harriman et al, Tetrahedr. Lett. 1995, 36(49), 8909-8912; or with reducing agents (Marder et al, Tetrahedr. 1995, 51(7), 1985-1994). Reactions of 13,14-enolization have not been described insofar, while rearrangement reactions in bases have been disclosed (Pinciroli et al., Tetrahedr. Lett. 1996, 37(52), 9365-9368; Yu and Liu, Tetrahedr. Lett. 1997, 38(23), 4133-4136).

According to a further aspect, the invention relates to a process for the 13,14 enolization of 13-ketobaccatin III to give intermediates sufficiently stable for further elaboration.

DETAILED DISCLOSURE OF THE INVENTION

The compounds of the invention have the following general formula III

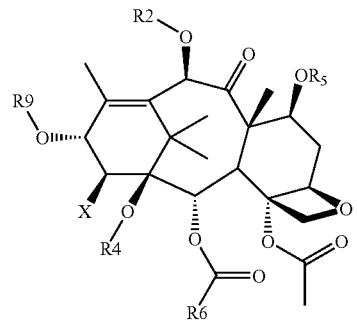

wherein
X is —$N_3$, —$NH_2$, —NH—$R_3$, =CH—$R_8$, or —O—$R_3$ when $R_6$ is different from phenyl,
$R_2$ is hydrogen or acyl;
$R_3$ is $C_1$-$C_4$ alkoxycarbonyl or, taken together with $R_4$, forms a carbonyl, thiocarbonyl, SO, $SO_2$ group;
$R_4$ is hydrogen or, taken together with $R_3$ or $R_8$, forms the groups specified in the respective definitions of $R_3$ and $R_8$;
$R_5$ is hydrogen or an alcohol-protecting group;
$R_6$ is aryl, substituted aryl, heteroaryl, with the proviso that it is different from phenyl when X is —O—$R_3$;
$R_8$ is hydrogen, $C_1$-$C_4$ alkyl, $C_1$-$C_4$ alkoxycarbonyl or, taken together with $R_4$, forms a carbonyl group;
$R_9$ is an acyl or hydroxyaminoacyl group.

The compounds of formula III can be prepared from compounds of formula II, in turn obtainable by conversion of 13-ketobaccatin III derivatives of formula I:

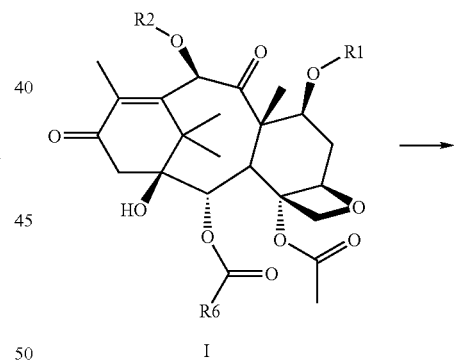

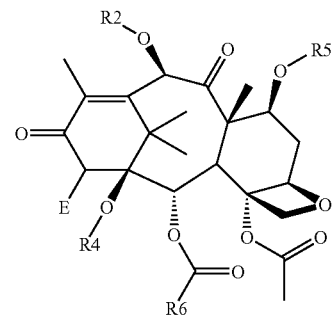

In formulae I and II,
$R_1$ is an alcohol-protecting group;

$R_2$ is an acyl group or an alcohol-protecting group;

E is —OH, —O—$R_3$, =$N_2$, —$N_3$, —$NH_2$, —NH—$R_3$, —NH—$NH_2$, —NH—N=N-Ts, —NH—N=N-Boc, —N($CO_2R_7$)$NHCO_2R_7$, =CH—$R_8$;

Ts is p-toluenesulfonyl;

$R_3$ is $C_1$-$C_4$ alkoxycarbonyl or, taken together with $R_4$, forms a carbonyl, thiocarbonyl, SO, $SO_2$ group;

$R_4$ is hydrogen or, taken together with $R_3$ or $R_8$, forms the groups specified in the respective definitions of $R_3$ and $R_8$;

$R_5$ is hydrogen or an alcohol-protecting group;

$R_6$ is aryl, substituted aryl, heteroaryl;

$R_7$ is a $C_1$-$C_4$ alkyl, aryl or arylalkyl group, $R_8$ is hydrogen, $C_1$-$C_4$ alkyl, $C_1$-$C_4$ alkoxycarbonyl or, taken together with $R_4$, forms a carbonyl group.

The compounds of formula III are useful for the treatment of neoplasias of various origin, in particular of tumors of such organs as ovary, breast, lung, colon, brain, as well as for the treatment of leukemias and melanoma.

In compounds of formulae I, II and III, an acyl group is preferably a straight or branched $C_2$-$C_6$ aliphatic acyl group, or a benzoyl group optionally substituted with one or more $C_1$-$C_4$ alkyl groups, $C_1$-$C_4$ alkoxy groups, halogens; aryl is preferably phenyl; substituted aryl is preferably phenyl substituted with one or more $C_1$-$C_4$ alkyl groups, $C_1$-$C_4$ alkoxy groups, halogens; heteroaryl is preferably 2-, 3- or 4-pyridyl, 2- or 3-furyl, 2- or 3-thenoyl; arylalkyl is preferably benzyl; a hydroxyaminoacyl group is preferably a β-isobutylisoserine or phenylisoserine residue substituted at the amino group with benzoyl or $C_1$-$C_4$ alkoxycarbonyl groups.

According to the present invention, compounds of formula II wherein E is —OH, =$N_2$, —$N_3$, —NH—N=N-Ts, —NH—N—N-Boc, —N($CO_2R_7$)$NHCO_2R_7$, =CH—$R_8$, can be obtained from suitable 13-ketobaccatin III protected derivatives of formula I through a process which is shown in the following scheme and involves:

a) treatment with bases to form an enolate of formula IV, wherein M is an alkali metal;

b) treatment of enolate IV with a suitable electrophile which can be converted to an E group to give a compound of formula II.

Scheme

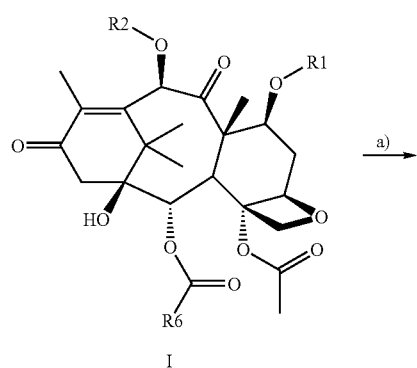

I

-continued

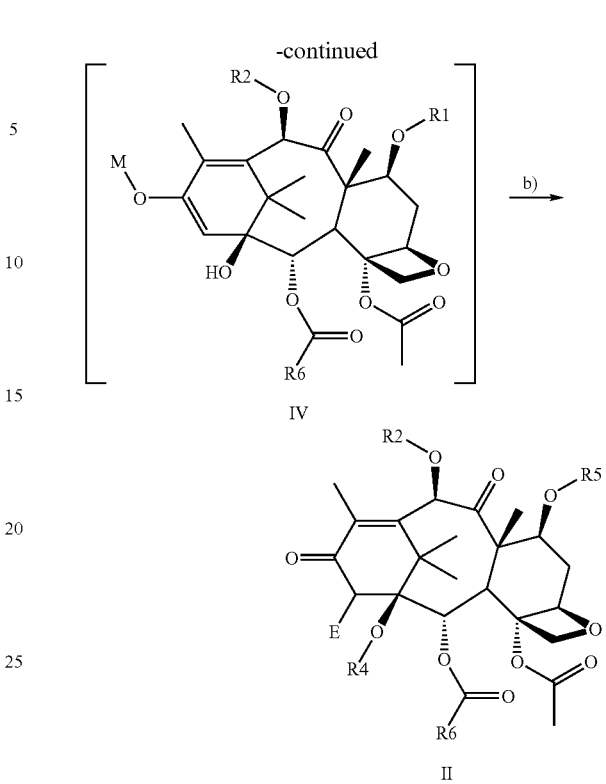

IV

II

Formation of enolate in step a) can be easily obtained by treatment of protected 13-ketobaccatin III with a base such as potassium t-butoxide, potassium bis(trimethylsilyl)amide, lithium diisopropyl amine in inert solvents such as tetrahydrofuran or diethyl ether, also in admixture with hexamethylphosphoramide (HMPA) or 1,3-dimethyl-3,4,5,6-tetrahydro-2[1H]-pyrimidinone (DMPU). The reaction is suitably carried out in a range of temperatures from −40 to −78° C.

Particularly preferred protective groups are silyl ethers, acetals, ethers, carbonates and carbamates.

Starting 13-ketobaccatin III (formula I) is easily obtainable from the appropriate protected baccatin by reaction with conventional oxidizers, as described in literature.

7-Protected 13-ketobaccatin III having different benzoate groups at the 2-position can be prepared according to the method by Ojima et al. (J. Am. Chem. Soc. 2000, 122, 5343-5353).

In the reported examples, $R_1$ is usually tert-butoxycarbonyl (Boc), triethylsilyl (TES) or 2-methoxypropane (MOP), and $R_2$ is usually acetyl, but other equivalent groups can be conveniently used to prepare similar compounds.

According to the scheme above, in step b) enolate IV is treated in situ with electrophiles such as oxaziridines (e.g. N-benzenesulfonyl phenyl oxaziridine, N-benzenesulfonyl m-nitrophenyl oxaziridine and camphorsulfonyloxaziridine), diazadicarboxylates (e.g. di-tert-butyl diazadicarboxylate and dibenzyl diazadicarboxylate), p-toluenesulfonylazide, t-butoxycarbonylazide, aldehydes (e.g. acetaldehyde, ethylglyoxylate) to give 13-ketobaccatine III of formula II wherein E is —OH, —NH—N=N-Ts, —NH—N=N-Boc, —N($CO_2R_7$)$NHCO_2R_7$, =CH—$R_8$.

When p-toluenesulfonylazide is used as the electrophile, the product wherein E is NH—N=N-Ts (or the N=N—NHTs tautomer) is obtained, besides decomposition products wherein E is $N_3$ or $N_2$. The quenching conditions of the reaction may be modulated to direct the reaction mainly to only one of the products. Thus, the tosylazido derivative can be recovered from the crude product by extraction with polar aprotic solvents such as dichloromethane or ethyl acetate. The diazo derivative is obtained upon stirring the reaction crude in polar aprotic solvents for reasonably long times, optionally under heating. The azido derivative is obtained by treating the reaction crude with protic agents, such as mixtures of acetic acid in THF with DMPU or HMPA, immediately after addition of the azide donor.

When ethyl glyoxylate is used as the electrophile, crotonic condensation with concomitant closure of the carbethoxy group at the C1 hydroxyl group takes place, to give an α,β-unsaturated γ-lactone.

In all cases, diastereoselection of the reaction is such that the E group is introduced mainly in 14β configuration.

Alternatively, enolate IV can be treated with silylating (e.g. tri-i-propyl silyl chloride), acylating (e.g. di-tert-butylpyrocarbonate), allcylating (e.g. dimethyl sulfate or methyl iodide) or phosphorylating agents thereby obtaining enol derivatives of formula V

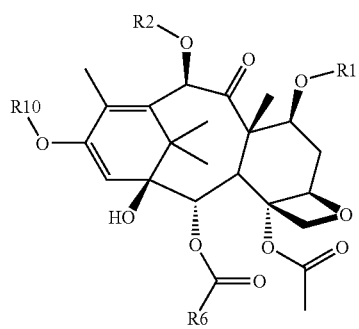

V wherein
$R_{10}$ is acyl, alkyl, trialkylsilyl or phosphate, and
$R_1$, $R_2$ and $R_6$ are as defined above.

Compounds V can also be easily obtained by enolization of ketone of formula II with particularly weak bases such as triethylamine or pyridine in aprotic solvents such as methylene chloride, toluene or mixtures thereof.

Compounds V can afford compounds of formula II by treatment with electrophiles in suitable conditions.

The groups introduced at the 14-position with the procedure described above can be further transformed to obtain other 13-ketobaccatin III derivatives functionalized at the 14-position.

Thus, compounds of formula II wherein E is —N(CO$_2$R$_7$)NHCO$_2$R$_7$ can be converted in the corresponding hydrazino derivatives (wherein E is —NH—NH$_2$) by decarboxylation according to conventional methods.

Compounds of formula II wherein E is —N$_3$ are easily reduced to amine (E=NH$_2$) by means of reductive systems such as triphenylphosphine in aqueous medium or H$_2$—Pd/C in a suitable solvent.

Compounds of formula II wherein E is —OH or —NH$_2$ can be treated with carbonating (e.g. carbonyldiimidazole, phosgene or triphosgene), thiocarbonating (e.g. thiocarbonyl diimidazole, thiophosgene) or sulforylating agents (e.g. sulforyl chloride or thionyl chloride), to obtain compounds of formula II wherein E is —OR$_3$ or —NHR$_3$. The reaction can be conveniently carried out in chlorinated solvents in the presence of a base (e.g. pyridine or triethylamine) in a range of temperatures from −40° C. to 70° C.

Alternatively, compounds of formula II wherein E is —OH or —NH$_2$ can be alkylated with such agents as alkyl halides or benzyl halides in the presence of weak bases.

Compounds of formula II are key intermediates for the synthesis of compounds of formula III of the invention. In particular, compounds III are obtainable from compounds of formula II wherein E is —O—R$_3$, —N$_3$, —NH—R$_3$, =CH—R$_8$, and R$_1$, R$_4$, R$_6$ are as defined above;

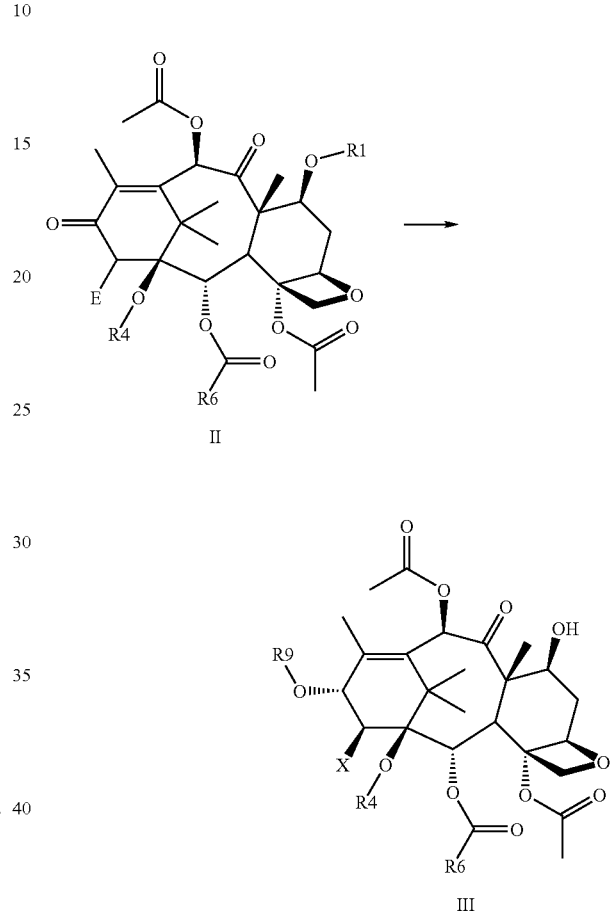

through a process which comprises:
a) reduction of the C13 carbonyl to give compounds of formula VII

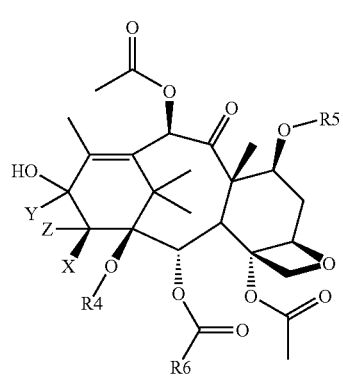

VII wherein

X is —O—R₃, —N₃, —NH—R₃, —CH₂—R₈;

Y and Z are hydrogen or, when X is —CH₂—R₈, are taken together to form a double bond;

and the other groups are defined as above;

b) esterification at the 13-position with derivatives of acids of formula IX to give compounds of formula VIII

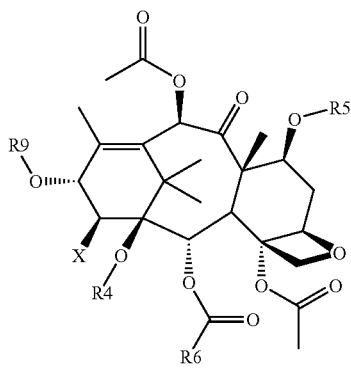

VIII wherein

R₄, R₅, R₆, R₉ are as defined above;

X is —O—R₃, —N₃, —NH—R₃, =CH—R₈;

c) optional cleavage of the protective groups.

Reduction of C13 ketone of step a) is carried out with suitable hydrides such as sodium borohydride, lithium borohydride, tetrabutylammonium borohydride, tetraethylammonium borohydride, sodium triacetoxy borohydride. The reaction can be carried out in a stoichiometric amount of reducing agent, although an excess is usually preferred. Depending on the used reducing agent, the reaction is carried out in alcohols, ethers, mixtures of alcohols and ethers or inert solvents, at temperatures ranging from −50 to 0° C.

C13 Esterification of step b) is usually carried out by action of carboxylic acids, or the corresponding salts, of formula IX

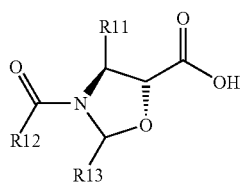

IX wherein

R₁₁ and R₁₃, which can be the same or different, are C₁-C₆ alkyl, aryl, or heteroaryl;

R₁₂ is C₁-C₆ alkyl, aryl, heteroaryl or C₁-C₄ alkoxy;

in the presence of condensing agents such as carbodiimides (e.g. dicyclohexylcarbodiimide or ethyl dimethylaminopropyl carbodiimide). Other known methods for the esterification at the 13-position of 7-protected baccatin III can also be successfully used.

Protective groups in step c) are removed under the conditions described in literature for the concerned protective group.

The most preferred carboxylic acid is the N-Boc-isobutylisoserine derivative of formula X

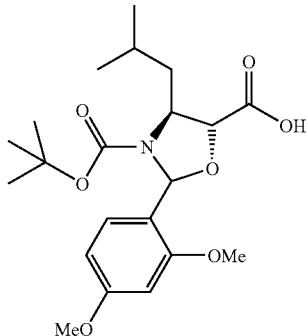

X

In this case, coupling with compounds of formula VII under the conditions illustrated in the examples yields compounds of formula XI

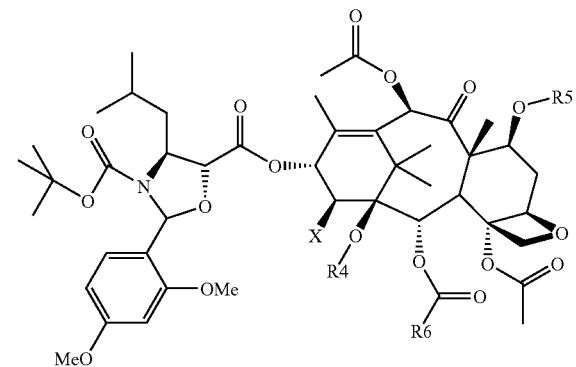

XI which by selective deprotection at the 7-position afford compounds of formula XII

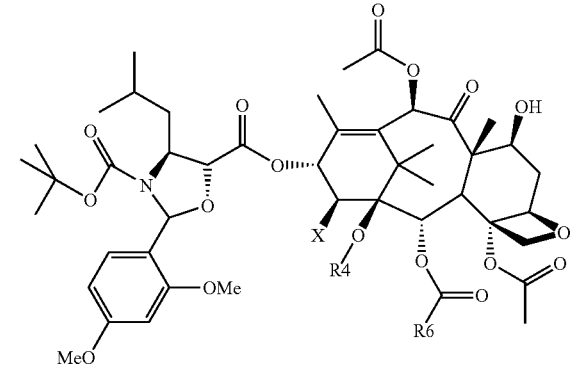

XII which are subjected to opening of the oxazolidine ring, to yield compounds of formula XIII

XIII

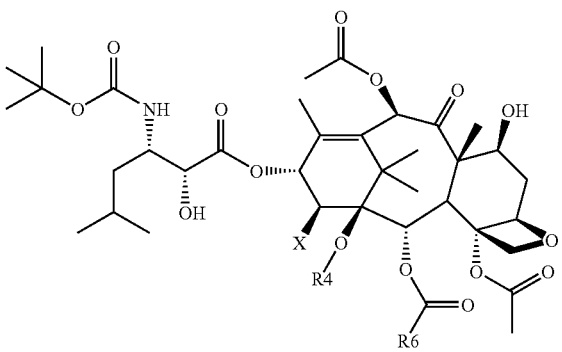

wherein
X, $R_3$, $R_4$, and $R_6$ are as defined above.

In case C13 esterification is carried out with the carboxylic acid of formula X, C7 deprotection is preferably effected before opening the oxazolidine.

Derivative of formula XI wherein X is —$N_3$ is particularly interesting, in that it is an useful intermediate for the preparation of compounds of formula XIV

XIV

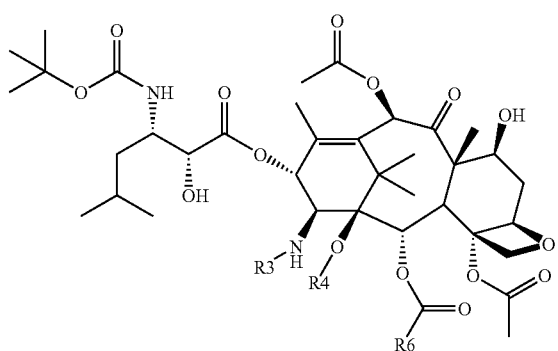

wherein
$R_3$ is hydrogen, acyl, alkyl or, taken together with $R_4$, forms a C=O, C=S, SO, $SO_2$ group;
$R_4$ is hydrogen or, taken together with $R_3$, forms a C=O, C=S, SO, $SO_2$ group;
according to an alternative preparation process to that described above, comprising:
a) reduction of the 14-azido group to give compounds of formula XV

XV

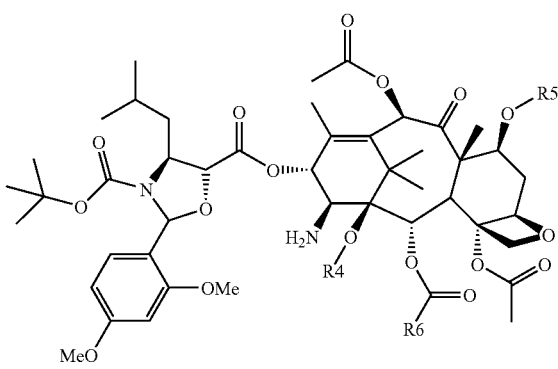

b) optional treatment with an acylating or alkylating agent to give compounds of formula XVI

XVI

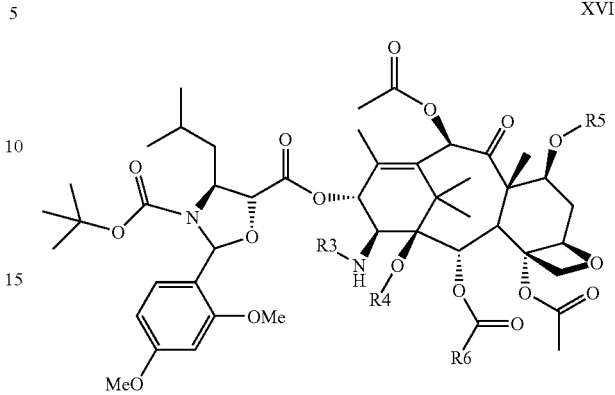

c) cleavage of the C7 protective group and opening of the oxazolidine to give compounds of formula XIV.

In the formulae XIV, XV and XVI, $R_3$, $R_4$, $R_5$ and $R_6$ have the same meanings as defined above.

For the envisaged therapeutical uses, compounds of formula III will be administered in the form of suitable pharmaceutical formulations, mainly through the parenteral route and at dosages in principle similar to those already used for some time in clinical practice with commercially available taxane derivatives (Paclitaxel and Docetaxel, for example).

The following examples illustrate the invention in greater detail.

EXAMPLE 1

7-Boc-13-ketobaccatin III

A solution of 13-ketobaccatin III (1.10 g, 1.9 mmol) in $CH_2Cl_2$ (0.5 mL) at 20° C. is added with carbon tetrachloride (14 ml). Partial precipitation of the baccatin derivative takes place. Subsequently, 1-methylimidazole (23 μL, 0.28 mmol) and di-tert-butyl-dicarbonate (1.03 g, 4.7 mmol) are added, under stirring and argon stream. After 8 hours, further 1-methyl-imidazole (16.0 μL, 0.20 mmol) is added. The solution is left at 25° C. for 24 hours, then solvent is evaporated off under reduced pressure. The oily residue is dissolved in a 1:1 acetone/water mixture (10 mL) and left at 20° C. for about 16 hours. The precipitate is filtered, washed with n-pentane and dried to give 1.12 g of the title product. Chromatography of mother liquors affords a further 0.12 g of product ($SiO_2$, n-hexane/EtOAc, 1.5:1.0). 1.24 g of product are thereby obtained (1.81 mmol, 95%). $[\alpha]_D^{20}=-35.6°$ (c 1.05, $CHCl_3$); IR ($CDCl_3$, $cm^{-1}$): 3483, 1731, 1676, 1371, 1274; $^1$H-NMR ($CDCl_3$, 400 MHz): δ=1.20 (s, 3H, Me), 1.22 (s, 3H, Me), 1.47 (s, 9H, 3Me), 1.76 (s, 3H, Me), 1.91 (m, 1H, Hβ-6, $J_1$=10.4 Hz, $J_2$=14.8 Hz, $J_3$=2.0 Hz), 1.92 (b, 1H, OH), 2.17 (s, 3H, Me), 2.19 (s, 3H, Me), 2.20 (s, 3H, Me), 2.64 (m, 1H, Hα-6, $J_1$=7.2 Hz, $J_2$=14.8 Hz, $J_3$=9.5 Hz), 2.66 (d, 1H, H-14, J=19.6 Hz), 2.94 (d, 1H, H-14, J=19.6 Hz), 4.02 (d, 1H, H-3, J=6.8 Hz), 4.09 (d, 1H, H-20, J=9.0 Hz), 4.32 (d, 1H, H-20, J=9.0 Hz), 4.94 (d, 1H, H-5, $J_1$=9.5 Hz, $J_2$=2.0 Hz), 5.39 (m, 1H, H-7, $J_1$=10.4 Hz, $J_2$=7.2 Hz), 5.67 (d, 1H, H-2, J=6.8 Hz), 6.57 (s, 1H, H-10), 7.44-7.50 (m, 2H, arom), 7.61-7.64 (m 1H, arom), 8.30 (d, 2H, arom); $^{13}$C-NMR ($CDCl_3$, 100 MHz): β=10.7, 14.0, 18.4, 21.0, 21.9, 27.9, 33.1, 33.6, 42.7, 46.7, 57.3, 72.8, 74.7, 76.3, 76.5, 77.4, 78.7, 80.5, 83.4, 84.0, 128.9, 129.0, 130.3, 134.3, 141.0, 152.4, 152.5, 167.0, 168.3, 170.3, 198.4, 200.5. Anal. Calc. $C_{36}H_{44}O_{13}$: C, 63.15; H, 6.48. Found: C, 63.39; H, 6.60.

EXAMPLE 2

7-TES-13-ketobaccatin III

13-Ketobaccatin III (5 g, 8.5 mmol), triethyl silyl chloride (3.6 mL, 21.4 mmol, 2.5 eq) and N-methylimidazole (2.73 mL, 34.3 mmol, 4 eq) are dissolved in anhydrous methylene chloride (25 mL). The solution is left under stirring for 1.5 h at room temperature, then quenched by carefully pouring it in a 2M $NaHSO_4$ solution (25 mL). The aqueous phase is repeatedly extracted with DCM (2×10 mL) and the combined organic phases are washed with brine (2×20 mL). The organic phase is dried over sodium sulfate and the solvent is evaporated off to give 4.7 g of the title product which is used directly in the subsequent step without further purification. M.p.: 212° C. TLC: cHex-AcOEt 1:1, Rf=0.57. $^1$H-NMR (200 MHz, $CDCl_3$): δ 0.58-0.66 (m, 6H, Si—$CH_2$), 0.90-0.98 (t, J=8.4, 9H, $CH_2CH_3$), 1.21 (s, 3H, 17-Me), 1.27 (s, 3H, 16-Me), 1.69 (s, 3H, 19-Me), 1.83-1.96 (m, 1H, 6-H), 2.20 (s, 3H, 18-Me), 2.21 (s, 3H, 10-OAc), 2.25 (s, 3H, 4-OAc), 2.48-2.65 (m, 1H, 6-H), 2.81 (ABq, 2H, 14-H), 3.93 (d, J=6.6, 1H, 3-H), 4.25 (ABq, 2H, 20-H), 4.51 (dd, J=10.6, 7.0, 1H, 7-H), 4.94 (d, J=7.7, 1H, 5-H), 5.72 (d, J=7.0, 1H, 2-H), 6.61 (s, 1H, 10-H), 7.52 (t, J=6.2, 2H, Bz), 7.64 (t, J=6.2, 1H, Bz), 8.10 (dd, J=7.4, 1.1, 2H, Bz).

EXAMPLE 3

14β-azido-7-Boc-13-ketobaccatin III

A solution of 7-Boc-13-ketobaccatin III (0.149 g, 0.22 mmol) in THF (1.8 mL) and DMPU (0.8 mL) is added in 2 minutes to a suspension of potassium tert-butoxide (0.064 g, 0.568 mmol) in anhydrous THF (1.5 mL) at −75° C., under nitrogen stream and strong stirring. After 15 min, 0.063 g (0.33 mmol) of tosylazide dissolved in 0.7 ml of THF are added in two minutes at −75° C. After two hours, temperature has raised to −50° C., the reaction is quenched by addition n of 0.057 mL (1.00 mmol) of glacial acetic acid. Temperature is slowly raised to 20° C. and after 19 hours the reaction mixture is diluted with 15 ml of $Et_2O$ and extracted with 10 ml of a $NH_4Cl$ aqueous saturated solution. The organic phases are washed three times with water, dried, filtered and evaporated under reduced pressure. Chromatography of the residue ($SiO_2$, n-hexane/EtOAc, 1.7:1.0) affords 0.080 g (0.10 mmol, 50%) of the title product. IR (KBr, $cm^{-1}$): 2976, 2935, 2122, 1731, 1272; $^1$H-NMR ($CDCl_3$, 400 MHz): δ=1.01 (s, 3H, Me), 1.22 (s, 3H, Me), 1.47 (s, 9H, 3Me), 1.81 (s, 3H, Me), 1.96 (m, 1H, Hβ-6, $J_1$=2.0 Hz, $J_2$=10.8 Hz, $J_3$=14.0 Hz), 2.19 (s, 3H, Me), 2.20 (s, 3H, Me), 2.24 (s, 3H, Me), 2.62 (m, 1H, Hα-6, $J_1$=7.2 Hz, $J_2$=9.6 Hz, $J_3$=14.0 Hz), 3.11 (s, 1H, OH), 3.98 (d, 1H, H-3, 6.8 Hz), 4.24 (d, 1H, H-20, J=8.4 Hz), 4.26 (s, 1H, H-14), 4.33 (d, 1H, H-20, J=8.4 Hz), 4.93 (d, 1H, H-5, $J_1$=2.0 Hz, $J_2$=9.6 Hz), 5.37 (m, 1H, H-7, $J_1$=10.8 Hz, $J_2$=7.2 Hz), 5.81 (d, 1H, H-2, J=6.8 Hz), 6.56 (s, 1H, H-10), 7.48-7.52 (m, 2H, arom), 7.60-7.66 (m 1H, arom), 8.02-8.05 (d, 2H, arom); $^{13}$C-NMR ($CDCl_3$, 100 MHz): 10.8, 14.4, 19.2, 20.9, 21.9, 27.9, 33.5, 33.7, 43.3, 45.8, 54.0, 57.2, 65.4, 72.5, 74.4, 75.5, 75.8, 76.1, 81.0, 83.5, 83.7, 129.1, 129.2, 130.0, 134.1, 138.8, 152.5, 153.8, 165.4, 168.2, 170.0, 196.6, 199.8. Anal. Calc $C_{36}H_{43}N_3O_{13}$: C, 59.58; H, 5.97. Found: C, 59.81; H, 5.85. MS mz 725.1 ($M^+$ calc $C_{36}H_{43}N_3O_{13}$ 725.7), 687.1, 670.0.

EXAMPLE 4

14-diazo-7-Boc-13-ketobaccatin III and 14-β-(1-p-toluenesulfonyl)triazenyl-7-Boc-13-ketobaccatin III A solution of 7-Boc-13-ketobaccatin III (0.03 g, 0.04 mmol) in THF (0.7 mL) and HMPA (0.2 mL) is added in 2 minutes to a suspension of potassium tert-butoxide (0.013 g, 0.04 mmol) in anhydrous THF (0.7 mL) at −75° C., under nitrogen stream and strong stirring. After 15 min, 0.013 g (0.07 mmol) of tosylazide dissolved in 0.2 ml of THF are added in two minutes at −75° C. After two hours, and after temperature has raised to −50° C., the reaction is quenched by addition of 5.0 ml of a $NH_4Cl$ saturated solution. Temperature is slowly raised to 20° C. and the reaction mixture is diluted with 3.0 ml of $Et_2O$ and extracted with 6.0 ml of a $NH_4Cl$ aqueous saturated solution. The organic phases are washed three times with water, dried, filtered and evaporated under reduced pressure. Chromatography of the residue ($SiO_2$, n-hexane/EtOAc, 1.7:1.0) affords 0.080 g (0.10 mmol, 45%) of 7-Boc-14-diazo-13-ketobaccatin III and 14β-(1-p-toluenesulfonyl)triazenyl-7-Boc-13-ketobaccatin III (0.025 g, 0.028 mmol, 13%) as a 3:1 mixture of tautomers.

14-diazo-7-Boc-13-ketobaccatin III: IR (KBr, $cm^{-1}$): 3500-3100, 2982, 2935, 2095, 1734, 1656, 1633, 1272; $^1$H-NMR ($CDCl_3$, 400 MHz): δ=1.23 (s, 3H, Me), 1.31 (s, 3H, Me), 1.48 (s, 9H, 3Me), 1.77 (s, 3H, Me), 1.92 (m, 1H, Hβ-6, $J_1$=1.5 Hz, $J_2$=10.8 Hz, $J_3$=14.0 Hz), 2.18 (s, 3H, Me), 2.19 (s, 3H, Me), 2.22 (s, 3H, Me), 2.63 (m, 1H, Hα-6, $J_1$=6.8 Hz, $J_2$=8.0 Hz, $J_3$=14.0 Hz), 4.04 (d, 1H, H-3, 6.4 Hz), 4.08 (d, 1H, H-20, J=8.4 Hz), 4.36 (d, 1H, H-20, J=8.4 Hz), 4.95 (d, 1H, H-5, $J_1$=1.5 Hz, $J_2$=8.0 Hz), 5.41 (m, 1H, H-7, $J_1$=10.8 Hz, $J_2$=6.8 Hz), 5.85 (d, 1H, H-2, J=7.2 Hz), 6.50 (s, 1H, H-10), 7.48-7.54 (m, 2H, arom), 7.62-7.68 (m 1H, arom), 8.40-8.80 (d, 2H, arom); $^{13}$C-NMR ($CDCl_3$, 100 MHz): 11.1, 14.4, 18.7, 21.0, 27.9, 32.9, 33.5, 43.0, 46.1, 56.6, 65.4, 73.7, 74.5, 76.2, 76.3, 79.5, 80.4, 83.5, 84.0, 128.3, 129.1, 130.4, 134.5, 141.1, 145.7, 152.5, 167.3, 168.3, 170.4, 184.1, 200.9. Anal. Calc. $C_{36}H_{42}N_2O_{13}$: C, 60.84; H, 5.96. Found: C, 60.71; H, 5.95. MS mz 710.2 ($M^+$ calcd for $C_{36}H_{42}N_2O_{13}$ 710.7), 687.1, 670.0.

14-β-(1-p-toluenesulfonyl)triazenyl-7-Boc-13-ketobaccatin III $^1$H-NMR ($CDCl_3$, 400 MHz, 21° C.): δ=1.26 (s, 3H, Me), 1.29 (s, 3H, Me), 1.43 (s, 9H, 3Me, minor), 1.46 (b, 9H, 3Me, major), 1.54 (s, 3H, Me), 1.67 (s, 3H, Me), 1.85 (m, 1H, Hβ-6, $J_1$=1.5 Hz, $J_2$=10.0 Hz, $J_3$=14.0 Hz), 2.05-2.18 (b, 9H, 3Me), 2.86 (m, 1H, Hα-6, $J_1$=7.0 Hz, $J_2$=8.0 Hz, $J_3$=14.0 Hz), 3.98 (d, 1H, H-3, J=11.0 Hz, minor), 4.10 (d, 1H, H-3, J=10.8 Hz, major), 4.39 (d, 1H, H-20, J=8.4 Hz), 4.61 (d, 1H, H-20, J=8.4 Hz), 4.87 (s, 1H), 4.95 (d, 1H, H-5, $J_1$=1.5 Hz, $J_2$=8.0 Hz), 5.34 (s, 1H), 5.51 (m, 1H, H-7, $J_1$=10.8 Hz, $J_2$=7.0 Hz), 5.78-5.88 (m, 1H, H-2, major, J=10.8 Hz and 1H, H-2, minor), 6.42-6.46 (b, 1H, H-10, major), 6.46-6.50 (b, 1H, H-10, minor), 7.28-7.32 (m, 2H, arom), 7.48-7.54 (m, 2H, arom), 7.62-7.68 (m 1H, arom), 7.79-7.82 (m, 2H, arom), 8.26-8.30 (d, 2H, arom).

EXAMPLE 5

14β-amino-7-Boc-13-ketobaccatin III

A solution of 0.04 g (0.05 mmol) of 14β-azido-7-Boc-13-ketobaccatin III in 1.5 ml of 7:3 acetonitrile-water is added with 0.013 g (0.05 mmol) of triphenylphosphine. After two hours the reaction mixture is concentrated under reduced pressure. Chromatography of the residue (SiO$_2$, n-hexane/EtOAc, 1.4:1.0) yields 0.024 g (0.03 mmol, 71%) of the title product. IR (KBr, cm$^{-1}$): 3500-3100, 3053, 2960, 1726, 1478, 1434, 1090; $^1$H-NMR (CDCl$_3$, 400 MHz): 0.89 (s, 3H, Me), 1.25 (s, 3H, Me), 1.48 (s, 9H, 3Me), 1.84 (s, 3H, Me), 1.98 (m, 1H, Hβ-6, J$_1$=2.1 Hz, J$_2$=10.8 Hz, J$_3$=14.4 Hz), 2.14 (s, 3H, Me), 2.19 (s, 3H, Me), 2.22 (s, 3H, Me), 2.61 (m, 1H, Hα-6, J$_1$=7.0 Hz, J$_2$=9.6 Hz, J$_3$=14.4 Hz), 3.58 (s, 1H, C14-H), 4.01 (d, 1H, H-3, 6.4 Hz), 4.26 (d, 1H, H-20, J=8.4 Hz), 4.33 (d, 1H, H-20, J=8.4 Hz), 4.94 (d, 1H, H-5, J$_1$=2.1 Hz, J$_2$=9.6 Hz), 5.40 (m, 1H, H-7, J$_1$=10.8 Hz, J$_2$=7.2 Hz), 5.86 (d, 1H, H-2, J=6.8 Hz), 6.55 (s, 1H, H-10), 7.44-7.50 (m, 2H, arom), 7.58-7.63 (m 1H, arom), 7.8-8.15 (d, 2H, arom); Anal. Calc C$_{36}$H$_{45}$NO$_{13}$: C, 61.79; H, 6.48. Found: C, 61.89; H, 6.42.

EXAMPLE 6

14β-azido-7-TES-13-ketobaccatin III

A solution of 1.40 g (2.0 mmol) of 7-TES-13-ketobaccatin III in 7.5 ml of THF and 3.7 ml of DMPU, under nitrogen stream, is added with 5.2 ml of a 1.0 M solution of potassium tert-butoxide in THF at −78° C. in two minutes and under strong stirring. After 10 min, 0.70 g (3.6 mmol) of tosylazide dissolved in 5.8 ml of THF is added very slowly at the same temperature. The reaction is quenched after 1 hour 30 minutes by addition of 0.5 mL (9.2 mmol) of acetic acid. Temperature spontaneously reaches room temperature. After 24 hours, the reaction mixture is diluted with 50 ml of Et$_2$O and extracted with 50 ml of a NH$_4$Cl aqueous saturated solution. The resulting organic phases are washed three times with H$_2$O, dried, filtered and concentrated under reduced pressure. Chromatography of the residue (SiO$_2$, n-hexane/EtOAc/Et$_2$O, 1.8: 0.7:0.4) affords 1.12 g (1.5 mmol, 76%) of the title product. IR (KBr, cm$^{-1}$): 3600-3100, 2956, 2878, 2117, 1730, 1370, 1238; $^1$H-NMR (CDCl$_3$, 400 MHz): δ=0.59 (m, 6H, 3CH$_2$), 0.93 (m, 9H, 3Me), 1.00 (s, 3H, Me), 1.27 (s, 3H, Me), 1.72 (s, 3H, Me), 1.91 (m, 1H, Hβ-6, J$_1$=2.2 Hz, J$_2$=10.7 Hz, J$_3$=14.2 Hz), 2.19 (s, 3H, Me), 2.22 (s, 3H, Me), 2.25 (s, 3H, Me), 2.54 (m, 1H, Hα-6, J$_1$=6.7 Hz, J$_2$=9.7 Hz, J$_3$=14.2 Hz), 3.09 (s, 1H, OH), 3.86 (d, 1H, H-3, J=6.7 Hz), 4.24 (d, 1H, H-20, J=8.6 Hz), 4.25 (s, 1H, CHN$_3$), 4.33 (d, 1H, H-20, J=8.6 Hz), 4.46 (m, 1H, H-7, J$_1$=10.7 Hz, J$_2$=6.7 Hz), 4.92 (d, 1H, H-5, J$_1$=2.0 Hz, J$_2$=9.5 Hz), 5.82 (d, 1H, H-2, J=6.9 Hz), 6.53 (s, 1H, H-10), 7.47-7.53 (m, 2H, arom), 7.60-7.65 (m 1H, arom), 8.02-8.04 (d, 2H, arom); $^{13}$C-NMR (CDCl$_3$, 100 MHz): 5.6, 7.2, 10.1, 14.4, 19.4, 21.2, 22.1, 34.0, 37.4, 43.4, 45.7, 59.6, 65.5, 72.5, 72.8, 75.5, 75.6, 76.3, 81.3, 84.0, 129.0, 129.2, 129.9, 134.0, 138.2, 155.4, 165.3, 169.0, 169.9, 196.5, 199.5. Anal. Calc. C$_{37}$H$_{49}$N$_3$O$_{11}$Si: C, 60.06; H, 6.68. Found: C, 59.87; H, 6.79. MS (mz) 740.0 (M$^+$ calc. C$_{37}$H$_{49}$N$_3$O$_{11}$Si 739.9), 700.2, 621.0, 242.3.

EXAMPLE 7

14-diazo-7-TES-13-ketobaccatin III and 14β-(1-p-toluenesulfonyl)triazenyl-7-TES-13-ketobaccatin III A solution of 0.22 g (0.32 mmol) of 7-TES-13-ketobaccatin III in 3.5 ml of THF and 0.6 ml of DMPU is slowly added, under strong stirring, with 0.8 ml of a 1.0 M solution of potassium tert-butoxide in THF at −78° C. After 15 min 0.11 g (0.58 mmol) of tosylazide dissolved in 0.9 ml of THF is added with a syringe at −70° C. Temperature is brought to −50° C. in 20 minutes. The reaction is quenched after 1 hour by addition of 4 ml of a NH$_4$Cl aqueous saturated solution. Temperature is brought to 20° C., the reaction mixture is diluted with 3 ml of Et$_2$O and extracted with 2 ml of NH$_4$Cl aqueous saturated solution. The organic phases are washed three times with H$_2$O, dried, filtered and concentrated under reduced pressure. Chromatography of the residue (SiO$_2$, n-hexane/EtOAc, 2.1:1.0) affords 0.092 g (0.13 mmol, 40%) of 7-TES-13-keto-14-diazo-baccatin III and 0.062 g (0.07 mmol, 23%) of 7-TES-13-keto-14β-(1-p-toluenesulfonyl)triazenyl-baccatin III as a tautomeric mixture.

14-diazo-7-TES-13-ketobaccatin III: IR (KBr, cm$^{-1}$): 3600-3100, 2956, 2881, 2098, 1727, 1629, 1370, 1270; $^1$H-NMR (CDCl$_3$, 400 MHz): δ=0.57 (m, 6H, 3CH$_2$), 0.91 (m, 9H, 3Me), 1.26 (s, 3H, Me), 1.28 (s, 3H, Me), 1.65 (s, 3H, Me), 1.85 (m, 1H, Hβ-6, J$_1$=2.2 Hz, J$_2$=10.7 Hz, J$_3$=14.2 Hz), 2.16 (s, 3H, Me), 2.20 (s, 3H, Me), 2.21 (s, 3H, Me), 2.53 (m, 1H, Hα-6, J$_1$=6.7 Hz, J$_2$=9.7 Hz, J$_3$=14.2 Hz), 3.89 (d, 1H, H-3, J=6.8 Hz), 4.07 (d, 1H, H-20, J=8.2 Hz), 4.33 (d, 1H, H-20, J=8.2 Hz), 4.47 (m, 1H, H-7, J$_1$=10.5 Hz, J$_2$=6.7 Hz), 4.92 (d, 1H, H-5, J$_1$=2.2 Hz, J$_2$=9.7 Hz), 5.84 (d, 1H, H-2, J=7.2 Hz), 6.50 (s, 1H, H-10), 7.42-7.50 (m, 2H, arom), 7.59-7.62 (m 1H, arom), 8.10-8.20 (d, 2H, arom); $^{13}$C-NMR (CDCl$_3$, 100 MHz): 5.7, 7.2, 10.4, 14.4, 18.9, 21.2, 22.0, 33.1, 37.4, 43.0, 45.9, 59.1, 69.6, 72.3, 74.0, 76.0, 76.5, 79.5, 80.6, 84.2, 127.7, 128.3, 129.0, 130.2, 130.4, 134.3, 140.4, 146.4, 167.0, 168.9, 170.3, 183.9, 200.6. Anal. Calc C$_{37}$H$_{48}$N$_2$O$_{11}$Si: C, 61.31; H, 6.67. Found: C, 61.39; H, 6.75.

14β-(1-p-toluenesulfonyl)triazenyl-7-TES-13-ketobaccatin III: IR (KBr, cm$^{-1}$): 3600-3100, 2957, 1728, 1625, 1615; $^1$H-NMR (CDCl$_3$, 400 MHz, 60° C.) relevant resonances at: δ=0.57-0.64 (m, 6H, 3CH$_2$), 0.90-0.96 (m, 9H, 3Me), 1.34 (s, 3H, Me), 1.44 (s, 3H, Me), 1.45 (s, 3H, Me), 1.89 (m, 1H, Hβ-6, J$_1$=3.3 Hz, J$_2$=10.8 Hz, J$_3$=13.9 Hz), 2.06-2.10 (b, 3H, Me), 2.10-2.14 (b, 3H, Me), 2.16-2.18 (b, 3H, Me), 2.39-2.44 (b, 3H, Me), 2.58 (m, 1H, Hα-6, J$_1$=6.3 Hz, J$_2$=9.5 Hz, J$_3$=13.9 Hz), 3.80-4.02 (b, 1H, H-3), 4.35 (d, 1H, H-20, J=8.8 Hz), 4.62 (d, 1H, H-20, J=8.8 Hz), 4.78 (m, 1H, H-7, J$_1$=10.8 Hz, J$_2$=6.3 Hz), 4.80 (s, 1H, H-14), 4.94 (d, 1H, H-5, J$_1$=3.3 Hz, J$_2$=9.5 Hz), 5.12-5.30 (b, 1H, NH), 5.80 (d, 1H, H-2, J=10.8 Hz), 6.66-6.70 (b, 1H, H-10), 7.24-7.30 (m, 2H, arom), 7.46-7.50 (m, 2H, arom), 7.58-7.60 (m 1H, arom), 7.78-7.82 (d, 2H, arom), 8.24-8.28 (d, 2H, arom); $^{13}$C-NMR (CDCl$_3$, 100 MHz) relevant resonances of the major tautomer at: 5.8 (3CH$_2$, minor), 6.1 (3CH$_2$, major), 7.04 (3Me, minor), 7.1 (3Me, major), 9.1, 20.8, 21.7, 21.8, 25.4, 26.5, 37.5, 42.7, 71.5, 74.7, 74.8, 78.3, 79.2, 84.3, 126.6, 127.5, 128.5, 128.9, 129.3, 129.7, 130.0, 130.7 (2CH), 133.7, 164.7, 168.5, 170.7, 202.2, 203.8.

EXAMPLE 8

14β-azido-7-TES-baccatin III

A solution of 0.46 g (0.63 mmol) of 14β-azido-7-TES-13-ketobaccatin III in 0.7 ml of THF and 12 ml of ethanol is added with 0.47 g (12.5 mmol) of sodium borohydride in small portions at −40° C. and under strong stirring. Temperature spontaneously raises to −28° C. After 4 days, the reaction is quenched by addition of 2 ml of acetic acid and extracted three times with 15 ml of ethyl acetate. The organic phases are dried, filtered and evaporated under reduced pressure. Chromatography of the crude (SiO$_2$, n-hexane/EtOAc, 2.1:1.0) affords 0.33 g (0.44 mmol, 70%) of the title product. IR (KBr, cm$^{-1}$): 3600-3300, 2956, 2881, 2112, 1728, 1371, 1233; $^1$H-NMR (CDCl$_3$, 400 MHz): δ=0.59 (m, 6H, 3CH$_2$), 0.93 (m, 9H, 3Me), 0.98 (s, 3H, Me), 1.24 (s, 3H, Me), 1.71 (s, 3H, Me), 1.90 (m, 1H, Hβ-6, J$_1$=2.1 Hz, J$_2$=10.7 Hz, J$_3$=14.2 Hz), 2.18 (s, 3H, Me), 2.20 (m, 3H, Me), 2.34 (s, 3H, Me), 2.53 (m, 1H, Hα-6, $J_1$=6.6 Hz, $J_2$=9.7 Hz, $J_3$=14.2 Hz), 2.82 (b, 1H, OH), 3.00 (s, 1H, OH), 3.82 (d, 1H, H-3, J=7.1 Hz), 3.98 (d, 1H, CHN$_3$, J=7.3 Hz), 4.23 (d, 1H, H-20, J=8.4 Hz), 4.33 (d, 1H, H-20, J=8.4 Hz), 4.46 (m, 1H, H-7, $J_1$=10.4 Hz, $J_2$=6.5 Hz), 4.80 (m, 1H, C13-H), 4.97 (d, 1H, H-5, $J_1$=1.9 Hz, $J_2$=9.5 Hz), 5.82 (d, 1H, H-2, J=7.1 Hz), 6.41 (s, 1H, H-10), 7.44-7.50 (m, 2H, arom), 7.58-7.62 (m 1H, arom), 8.07-8.1 (d, 2H, arom); $^{13}$C-NMR (CDCl$_3$, 100 MHz): 5.7, 7.2, 10.4, 15.2, 21.3, 22.1, 22.8, 26.6, 30.1, 37.5, 43.3, 46.8, 59.0, 68.8, 72.5, 74.6, 75.4, 75.7, 76.6, 76.9, 81.3, 84.3, 128.8, 129.4, 130.1, 133.8, 134.3, 140.9, 165.8, 169.4, 170.4, 201.4. Anal. Calc. C$_{37}$H$_{51}$N$_3$O$_{11}$Si: C, 59.90; H, 6.93. Found: C, 60.16; H, 6.89.

EXAMPLE 9

13-[N-Boc-N,O-(2,4-dimethoxybenzylidene)-β-isobutylisoserinoyl]-14β-azido-7-TES-baccatin III A solution of 0.074 g (0.18 mmol) of N-Boc-N,O-(2,4-dimethoxybenzylidene)-β-isobutylisoserine acid in 5 ml of toluene, cooled to 0° C., is added under nitrogen stream and stirring, with 0.08 g (0.11 mmol) of 7-TES-14β-azido-baccatin III, 0.04 g (0.18 mmol) of dicyclohexylcarbodiimide (DCC), 0.01 g (0.12 mmol) of dimethylaminopyridine (DMAP), and 0.003 g (0.02 mmol) of p-toluenesulfonic acid (PTSA). After 1 hour a 70° C. the reaction mixture is cooled and filtered and the solid is washed three times with dichloromethane; the combined organic phases are subsequently evaporated under reduced pressure. Chromatography of the reaction crude (SiO$_2$, n-hexane/EtOAc, 2.2:1.0) affords 0.089 g (0.08 mmol, 72%) of the title product. IR (KBr, cm$^{-1}$): 3491, 2957, 2111, 1731, 1614, 1508, 1368; $^1$H-NMR (CDCl$_3$, 400 MHz) relevant resonances at: δ=0.59 (m, 6H, 3CH$_2$), 0.93 (m, 9H, 3Me), 1.71 (s, 3H, Me), 1.91 (m, 1H, Hβ-6, $J_1$=2.0 Hz, $J_2$=11.2 Hz, $J_3$=14.0 Hz), 2.11 (s, 3H, Me), 2.19 (s, 3H, Me), 2.33 (s, 3H, Me), 2.52 (m, 1H, Hα-6, $J_1$=6.8 Hz, $J_2$=9.6 Hz, $J_3$ 14.0 Hz), 3.83 (d, 1H, H-3), 3.83 (s, 3H, OMe), 3.87 (s, 3H, OMe), 4.04 (d, 1H, H-14, J=8.8 Hz), 4.24 (d, 1H, H-20, J=8.0 Hz), 4.32 (d, 1H, H-20), 4.94 (m, 1H, H-5), 5.88 (d, 1H, H-2, J=7.6 Hz), 6.25 (d, 1H, H-13, J=8.8 Hz), 7.44-7.50 (m, 2H, arom), 7.58-7.62 (m 1H, arom), 8.07-8.1 (d, 2H, arom). Anal. Calc. C$_{58}$H$_{80}$N$_4$O$_{17}$Si: C, 61.47; H, 7.11. Found: C, 60.89; H, 7.34.

EXAMPLE 10

13-(N-Boc-β-isobutylisoserinoyl)-14β-azido-baccatin III

A solution of 0.080 g (0.07 mmol) of 13-[N-Boc-N,O-(2,4-dimethoxybenzylidene)-β-isobutylisoserinoyl]-14β-azido-7-TES-baccatin III in 2 ml of acetonitrile and 2 ml of pyridine is added, at 0° C., with 0.8 mL (0.1 mL/10 mg of substrate) of hydrofluoric acid-pyridine. After half an hour, the temperature is brought to 25° C. After three hours the reaction is quenched by addition of 4 ml of a NH$_4$Cl saturated solution and extracted three times with 8 ml of AcOEt. The organic phases are washed three times with a CuSO$_4$ aqueous saturated solution, dried, filtered, and evaporated under reduced pressure. The resulting reaction crude (dissolved in 1.5 ml of dichloromethane) is added at 0° C. with 0.7 ml of a 0.1 M solution of acetyl chloride in MeOH. After three hours the reaction is quenched by addition of 3 ml of a NH$_4$Cl aqueous saturated solution. The organic phases are dried, filtered, and evaporated under reduced pressure. Chromatography (SiO$_2$, n-hexane/EtOAc, 1.0:1.2) yields 0.04 g (0.05 mmol, 70%) of the title product. IR (KBr, cm$^{-1}$): 3461, 2110, 1734, 1636, 1373, 1242, 1048; $^1$H-NMR (CDCl$_3$, 400 MHz): δ=0.97 (t, 6H, 2Me), 1.19 (s, 3H, Me), 1.20 (s, 3H, Me), 1.38-1.4 (br s., 1H), 1.68-1.74 (m, 1H, H-5'), 1.71 (s, 3H, Me), 1.88 (s, 3H, Me), 1.91 (m, 1H, Hβ-6, $J_1$=2.3 Hz, $J_2$=10.7 Hz, $J_3$=14.8 Hz), 2.24 (s, 3H, Me), 2.43 (s, 3H, Me), 2.46-2.52 (b, 1H, OH), 2.57 (m, 1H, Hα-6, $J_1$=6.6 Hz, $J_2$=9.6 Hz, $J_3$=14.9 Hz), 3.76 (d, 1H, H-3, J=7.1 Hz), 3.85 (d, 1H, OH), 4.04 (d, 1H, H-14, J=8.8 Hz), 4.08 (m, 1H, H-3'), 4.26 (d, 1H, H-20, J=8.8 Hz), 4.35 (d, 1H, H-20), 4.39 (m, 1H, H-7), 4.72 (d, 1H, H-2'), 4.98 (m, 1H, H-5, $J_1$=2.3 Hz, $J_2$=9.6 Hz), 5.88 (d, 1H, H-2, J=7.1 Hz), 6.07 (d, 1H, H-13, J=8.8 Hz), 6.28 (s, 1H, H-10), 7.44-7.50 (m, 2H, arom), 7.58-7.62 (m 1H, arom), 8.07-8.1 (d, 2H, arom); $^{13}$C-NMR (CDCl$_3$, 100 MHz): 10.0, 15.3, 21.3, 22.3, 22.7, 23.6, 23.7, 25.1, 27.1, 28.6, 35.9, 40.8, 43.5, 45.3, 52.0, 59.0, 65.5, 72.3, 74.1, 74.8, 75.5, 76.5, 77.2, 77.6, 80.5, 81.6, 84.5, 128.9, 129.1, 130.1, 133.9, 134.9, 139.1, 156.2, 165.7, 170.0, 171.1, 173.4, 202.9. Anal. Calc. C$_{39}$H$_{53}$NO$_{11}$Si: C, 62.70; H, 7.34. Found: C, 62.36; H, 7.49.

EXAMPLE 11

14β-amino-7-TES-13-ketobaccatin III

A solution of 0.08 g (0.11 mmol) of 14β-azido-7-TES-13-ketobaccatin III in 3.2 ml of an acetonitrile/water 9/1 mixed solution is added with 0.03 g (0.12 mmol) of triphenylphosphine. The reaction is cooled at 5° C., and after 18 hours is evaporated under reduced pressure. Chromatography of the residue (SiO$_2$, n-hexane/EtOAc/Et$_{2o}$, 1.8:0.7:0.3) affords 0.07 g (0.11 mmol, 97%) of the title product: IR (KBr, cm$^{-1}$): 3500-3100, 3053, 1730, 1438, 1239, 1063; $^1$H-NMR (CDCl$_3$, 400 MHz): δ=0.58 (m, 6H, 3CH$_2$), 0.84 (s, 3H, Me), 0.93 (m, 9H, 3Me), 1.27 (s, 3H, Me), 1.73 (s, 3H, Me), 1.90 (m, 1H, Hβ-6, $J_1$=2.0 Hz, $J_2$=11.2 Hz, $J_3$=14.0 Hz), 2.12 (s, 3H, Me), 2.19 (m, 3H, Me), 2.21 (s, 3H, Me), 2.52 (m, 1H, Hα-6, $J_1$=6.4 Hz, $J_2$=9.2 Hz, $J_3$=14.0 Hz), 3.57 (s, 1H, H-14), 3.84 (d, 1H, H-3, J=6.8 Hz), 4.24 (d, 1H, H-20, J=8.8 Hz), 4.30 (d, 1H, H-20, J=8.8 Hz), 4.47 (m, 1H, H-7, $J_1$=10.4 Hz, $J_2$=6.4 Hz), 4.89 (d, 1H, H-5, $J_1$=2 Hz, $J_2$=9.6 Hz), 5.86 (d, 1H, H-2, J=6.8 Hz), 6.50 (s, 1H, H-10), 7.43-7.45 (m, 2H, arom), 7.61-7.66 (m 1H, arom), 7.99-8.01 (d, 2H, arom); Anal. Calcl. C$_{43}$H$_{58}$N$_4$O$_{15}$Si: C, 59.30; H, 6.71. Found: C, 60.3; H, 7.19.

EXAMPLE 12

14β-Amino-7-TES-13-ketobaccatin III 14,1-carbamate

A solution of 0.18 g (0.26 mmol) of 14β-amino-7-TES-13-ketobaccatin III in 6 mL of CH$_2$Cl$_2$ at −78° C. is added with 0.13 mL (0.26 mmol) of a 1.93 M solution of phosgene in toluene and 0.04 mL (0.51 mmol) of pyridine under stirring. After 1 hour the reaction mixture is quenched by addition of 5 ml of water and extracted with 10 ml of dichloromethane; the organic phases are washed three times with brine, dried, filtered, and evaporated under reduced pressure. Chromatography (SiO$_2$, n-hexane/EtOAc/Et$_{2o}$, 1.8:0.7:0.3) affords 0.16 g (0.22 mmol, 86%) of the title product. IR (KBr, cm$^{-1}$): 3342, 2955, 1731, 1452, 1238, 1090; $^1$H-NMR (CDCl$_3$, 400 MHz): δ=0.60 (m, 6H, 3CH$_2$), 0.93 (m, 9H, 3Me), 1.14 (s, 3H, Me), 1.34 (s, 3H, Me), 1.73 (s, 3H, Me), 1.92 (m, 1H, Hβ-6, $J_1$=2.4 Hz, $J_2$=10.8 Hz, $J_3$=14.0 Hz), 2.15 (s, 3H, Me), 2.20 (m, 3H, Me), 2.22 (s, 3H, Me), 2.52 (m, 1H, Hα-6, $J_1$=6.6 Hz, $J_2$=9.7 Hz, $J_3$=14.0 Hz), 3.83 (d, 1H, H-3, J=6.8 Hz), 4.17 (s, 1H, H-14), 4.23 (d, 1H, H-20, J=8.8 Hz), 4.32 (d, 1H, H-20, J=8.8 Hz), 4.46 (m, 1H, H-7, $J_1$=10.7 Hz, $J_2$=6.5 Hz), 4.90 (d, 1H, H-5, $J_1$=1.9 Hz, $J_2$=9.5 Hz), 6.02 (s, 1H, N—H), 6.06 (d, 1H, H-2, J=6.9 Hz), 6.48 (s, 1H, H-10), 7.42-7.45 (m, 2H, arom), 7.58-7.61 (m 1H, arom), 7.96-7.98 (d, 2H, arom); $^{13}$C-NMR (CDCl$_3$, 100 MHz): 5.7, 7.2, 10.4, 14.2, 19.8 21.1, 22.1, 30.1, 32.9, 37.3, 42.6, 45.4, 59.2, 59.3, 69.7, 72.3, 74.9, 76.3, 80.9, 84.2, 86.2, 128.4, 129.0, 129.9, 134.2, 138.9, 151.1, 155.7, 164.6, 168.9, 170.1, 195.6, 199.3. Anal. Calc. C$_{39}$H$_{51}$NO$_{12}$Si: C, 62.13; H, 6.82. Found: C, 60.16; H, 6.89.

EXAMPLE 13

14β-amino-7-TES-baccatin III 14,1-carbamate

A solution of 0.07 g (0.1 mmol) of 14β-amino-7-TES-13-ketobaccatin III 14,1-carbamate in 4 ml of ethanol at −40° C. is added, under stirring, with 0.056 g (1.49 mmol) of sodium borohydride. Temperature is brought to −18° C. then, after 4 hours, a further 0.04 g (1.0 mmol) of sodium borohydride is added. After 18 hours, the reaction mixture is quenched by addition of 2 ml of acetic acid and extracted with 10 ml of ethyl acetate. The organic phases are dried, filtered, and evaporated under reduced pressure. $^1$H-NMR spectrum of the residue shows the presence of 14β-amino-7-TES-baccatin III 14,1-carbamate and of its 13β epimer in an α/β=62/38 ratio. Chromatography of the mixture (SiO$_2$, dichloromethane/ EtOAc, 1.0:0.9) yields 0.04 g (0.06 mmol, 62%) of the title product. $^1$H-NMR (CDCl$_3$, 400 MHz): δ=0.58 (m, 6H, 3CH$_2$), 0.93 (m, 9H, 3Me), 1.08 (s, 3H, Me), 1.26 (s, 3H, Me), 1.70 (s, 3H, Me), 1.88 (m, 1H, Hβ-6, J$_1$=2.0 Hz, J$_2$=10.0 Hz, J$_3$=13.2 Hz), 2.15 (s, 3H, Me), 2.17 (m, 3H, Me), 2.19 (s, 3H, Me), 2.52 (m, 1H, Hα-6, J$_1$=7.2 Hz, J$_2$=9.6 Hz, J$_3$=14.0 Hz), 3.66 (b, 1H, OH), 3.75 (d, 1H, H-3, J=7.2 Hz), 3.98 (d, 1H, H-14 J=6.0 Hz), 4.15 (d, 1H, H-20, J=8.4 Hz), 4.23 (d, 1H, H-20, J=8.4 Hz), 4.44 (m, 1H, H-7, J$_1$=10.0 Hz, J$_2$=6.0 Hz), 4.66 (m, 1H, H-13), 4.93 (d, 1H, H-5, J$_1$=2.0 Hz, J$_2$=8 Hz), 5.98 (d, 1H, H-2, J=7.2 Hz), 6.42 (s, 1H, H-10), 7.41-7.45 (m, 2H, arom), 7.58-7.61 (m 1H, arom), 7.98-8.01 (d, 2H, arom); $^{13}$C-NMR (CDCl$_3$, 100 MHz): 5.7, 7.2, 10.6, 15.1, 21.3, 22.1, 22.6, 26.2, 30.1, 37.4, 42.2, 46.5, 58.9, 61.1, 71.1, 72.3, 73.4, 75.4, 80.7, 84.3, 88.9, 128.8, 128.9, 129.9, 132.5, 134.0, 143.1, 158.2, 165.3, 169.2, 170.3, 201.3. Anal. Calc. C$_{39}$H$_{53}$NO$_{12}$Si: C, 61.97; H, 7.07. Found: C, 62.3; H, 6.93.

EXAMPLE 14

13-[N-Boc-N,O-(2,4-dimethoxybenzylidene)-β-isobutylisoserinoyl]-14β-amino-7-TES-baccatin II 14,1-carbamate A solution of 0.124 g (0.30 mmol) of N-Boc-N,O-(2,4-dimethoxybenzylidene)-β-isobutylisoserine in 6 ml of toluene, cooled at 0° C., is added with 0.102 g (0.14 mmol) of 7-TES-14β-amino-baccatin III 14,1-carbamate, 0.06 g (0.30 mmol) of dicyclohexylcarbodiimide (DCC), 0.02 g (0.15 mmol) of dimethylaminopyridine (DMAP), and 0.005 g (0.03 mmol) of p-toluenesulfonic acid (PTSA), under stirring and nitrogen stream. After 2 hours at 70° C., a further 0.045 g (0.11 mmol) of N-Boc-N,O-(2,4-dimethoxybenzylidene)-β-isobutylisoserine and 0.022 g (0.11 mmol) of DCC are added. After a further 3 hours, the reaction is cooled and filtered. The solid is washed three times with dichloromethane; the combined organic phases are subsequently concentrated under reduced pressure. Chromatography of the reaction mixture (SiO$_2$, n-hexane/EtOAc/CH$_2$Cl$_2$, 1.0:0.6:0.6) yields 0.136 g (0.12 mmol, 86%) of the title product. IR (KBr, cm$^{-1}$): 3435, 2956, 1735, 1454, 1369, 1235; $^1$H-NMR (CDCl$_3$, 400 MHz) relevant resonances: δ=0.58 (m, 6H, 3CH$_2$), 0.93 (m, 9H, 3Me), 1.75 (s, 3H, Me), 2.19 (s, 3H, Me), 2.26 (s, 3H, Me), 2.52 (m, 1H, Hα-6, J$_1$=6.4 Hz, J$_2$=10.0 Hz, J$_3$=14.4 Hz), 3.87 (s, 3H, OMe), 3.88 (s, 3H, OMe), 4.22 (d, 1H, H-20, J=7.6 Hz), 4.26 (d, 1H, H-20), 4.90 (m, 1H, H-5, J=7.2 Hz) 6.05 (d, 1H, H-2, J=7.2 Hz), 7.40-7.44 (m, 2H, arom), 7.56-7.60 (m 1H, arom), 7.98-7.99 (d, 2H, arom). Anal. Calc. C$_{59}$H$_{80}$N$_2$O$_{18}$Si: C, 62.53; H, 7.11. Found: C, 63.3; H, 6.99.

EXAMPLE 15

13-(N-Boc-β-isobutylisoserinoyl)-14β-amino-baccatin III 14,1-carbamate

A solution of 0.114 g (0.10 mmol) of 13-[N-Boc-N,O-(2,4-dimethoxybenzylidene)-β-isobutylisoserinoyl]-14β-amino-7-TES-baccatin III 14,1-carbamate in 1.6 ml of dichloromethane is added, at 0° C., with 1.02 ml of a 0.01 M acetyl chloride solution in methanol. After 24 hours at 5° C., the reaction mixture is quenched by addition of 7 ml of a NH$_4$Cl aqueous saturated solution and extracted with 10 ml of AcOEt. The combined organic phases are subsequently dried and concentrated under reduced pressure. The chromatographic purification (SiO$_2$, n-hexane/EtOAc/Et$_2$O 1:0.7:0.3) affords 0.06 g (0.061 mmol, 66%) of the title compound. $^1$H-NMR (CDCl$_3$, 400 MHz): δ=0.97 (t, 6H, 2Me), 1.25-1.31 (b, 8H, 2Me and 2H of H-4'), 1.37 (s, 9H, 3Me), 1.69-1.72 (s, 4H, Me, H-5'), 1.78-1.96 (m, 4H, Hβ-6, Me), 2.25 (s, 3H, Me), 2.33 (s, 3H, Me), 2.55 (m, 1H, Hα-6), 3.05 (d, 1H, OH, J=6.4 Hz), 3.76 (d, 1H, H-3, J=7.2 Hz), 4.15-4.22 (m, 3H, H-14, H-2', H3'), 4.28 (d, 1H, H-20), 4.35 (d, 1H, H-20), 4.38 (m, 1H, H-7), 4.73 (d, 1H, N'—H, J=9.6 Hz), 4.94 (m, 1H, H-5, J$_1$=0.8 Hz, J$_2$=7.6 Hz), 6.02 (d, 1H, H-2, J=7.6 Hz), 6.11 (d, 1H, H-13, J=6.8 Hz, J=1.6 Hz), 6.26 (s, 1H, H-10), 7.42-7.45 (m, 2H, arom), 7.54-7.58 (m 1H, arom), 8.02-8.1 (d, 2H, arom); $^{13}$C-NMR (CDCl$_3$, 100 MHz) relevant resonances: 10.2, 15.4, 21.2, 21.8, 22.9, 23.4, 23.8, 25.0, 26.3, 28.7, 30.1, 35.8, 41.8, 42.5, 44.9, 51.8, 57.8, 58.8, 71.2, 72.1, 73.0, 75.3, 76.4, 81.2, 81.7, 84.4, 128.7, 128.9, 130.0, 134.0, 134.1, 140.1, 156.4, 164.9, 173.5, 202.5; Anal. Calc. C$_{44}$H$_{58}$N$_2$O$_{16}$: C, 60.68; H, 6.71. Found: C, 61.2; H, 6.99.

EXAMPLE 16

13-[N-Boc-N,O-(2,4-dimethoxybenzylidene)-β-isobutylisoserinoyl]-7-TES-14β-amino-baccatin III A catalytic amount of palladium on charcoal is added to a solution of 0.052 g (0.05 mmol) 13-[N-Boc-N,O-(2,4-dimethoxybenzylidene)-β-isobutylisoserinoyl]-14β-azido-7-TES-baccatin III in 2.0 ml of MeOH, then gas hydrogen is bubbled therein. After 18 hours at room temperature, the reaction mixture is filtered through celite bed, and the solid is washed with 6 ml of ethyl acetate. The resulting organic phases are heated to 45° C. for 20 minutes and subsequently evaporated under reduced pressure. Chromatography of the residue (SiO$_2$, n-hexane/EtOAc/CH$_2$Cl$_2$ 0.7:0.3:1.0) yields 0.72 g (0.064 mmol, 70%) of the title product. IR (KBr, cm$^{-1}$): 3449, 2957, 1726, 1617, 1368, 1237, 1105; $^1$H-NMR (CDCl$_3$, 400 MHz) relevant resonances at δ=0.58 (m, 6H, 3CH$_2$), 0.94 (m, 9H, 3Me), 1.07 (m, 10H), 1.72 (s, 3H, Me), 2.12 (s, 3H, Me), 2.18 (s, 3H, Me), 2.30 (s, 3H, Me), 2.51 (m, 1H, Hα-6), 3.35 (d, 1H, J=8.8 Hz), 3.83 (s, 3H, OMe), 3.88 (s, 3H, OMe), 4.26 (m, 2H, 2H-20), 4.53 (m, 3H), 4.93 (d, 1H, H-5), 5.85 (d, 1H, H-2, J=7.2 Hz), 6.06 (d, 1H, H-13), 6.45-6.51 (m, 3H), 6.59 (s, 1H, H-10), 7.42-7.45 (m, 2H, arom), 7.54-7.60 (m 1H, arom), 8.00-8.02 (d, 2H, arom). Anal. Calc. C$_{58}$H$_{82}$N$_2$O$_{17}$Si: C, 62.91; H, 7.46. Found: C, 63.4; H, 6.87.

EXAMPLE 17

13-(N-Boc-β-isobutylisoserinoyl)-14β-amino-baccatin III

A solution of 0.107 g (0.09 mmol) of 13-[N-Boc-N,O-(2,4dimethoxybenzylidene)-β-isobutylisoserinoyl]-7-TES-14β-amino-baccatin III in 2.7 ml of acetonitrile and 2.7 ml of pyridine is added, at 0° C., with 10.7 mL (0.1 mL/10 mg of substrate) hydrofluoric acid-pyridine. After half an hour the temperature is brought to 25° C. After three hours, the reaction is quenched by addition of 6 ml of a $NH_4Cl$ aqueous saturated solution and extracted three times with 8 ml of AcOEt. The organic phases are washed three times with a $CuSO_4$ aqueous saturated solution, dried, filtered, and evaporated under reduced pressure. The resulting reaction crude is dissolved in 3.5 ml of dichloromethane, then added, at 0° C., with 1.15 ml of a 0.1 M acetyl chloride solution in MeOH. After three hours, the reaction is quenched by addition of 5 ml of a $NH_4Cl$ aqueous saturated solution and extracted with 8 ml of AcOEt. The organic phases are dried, filtered, and evaporated under reduced pressure. Chromatography ($SiO_2$, n-hexane/EtOAc, 1.0:1.2) yields 0.05 g (0.06 mmol, 70%) of the title product. $^1$H-NMR ($CDCl_3$, 400 MHz): δ=1.00 (m, 6H, 2Me), 1.14 (s, 3H, Me), 1.19 (s, 3H, Me), 1.32 (s, 9H, 3Me), 1.62-1.78 (s, 4H, Me, H-5'), 1.84-1.94 (m, 4H, Hβ-6, Me), 2.24 (s, 3H, Me), 2.39 (s, 3H, Me), 2.55 (m, 1H, Hα-6, $J_1$=6.4 Hz, $J_2$=9.6 Hz, $J_3$=14.8 Hz), 3.09 (b, 1H, OH), 3.35 (d, 1H, J=9.2 Hz), 3.74 (d, 1H, J=7.2 Hz), 4.18-4.33 (m, 4H, H-2', H3', 2H-20), 4.41 (m, 1H, H-7), 4.70 (d, 1H, N'—H, J=9.6 Hz), 4.95 (m, 1H, H-5, $J_1$=2 Hz, $J_2$=9.6 Hz), 5.81 (d, 1H, H-2, J=7.6 Hz), 5.90 (d, 1H, H-13, J=9.2 Hz, J=1.2 Hz), 6.27 (s, 1H, H-10), 7.42-7.46 (m, 2H, arom), 7.52-7.61 (m 1H, arom), 8.0-8.06 (d, 2H, arom); $^{13}$C NMR ($CDCl_3$, 100 MHz): 10.1, 15.3, 21.3, 22.3, 23.0, 23.7, 24.4, 25.1, 26.8, 28.6, 30.1, 35.8, 42.2, 43.3, 45.0, 51.4, 53.5, 58.7, 72.3, 72.9, 75.1, 75.3, 75.7, 80.6, 81.5, 84.5, 128.8, 129.8, 130.0, 133.4, 135.0, 138.8, 156.1, 165.6, 169.8, 171.4, 203.3, MS (mz) ($M^+$ calc. $C_{43}H_{60}N_2O_{15}$ 844.4), 845.4, 789.5, Anal. Calc. $C_{43}H_{60}N_2O_{15}$: C, 61.12; H, 7.16. Found: C, 62.3; H, 6.99.

EXAMPLE 18

13-[N-Boc-N,O-(2,4-dimethoxybenzylidene)-β-isobutylisoserinoyl]-7-TES-14β-t-butoxycarbamoyl-baccatin III 14,1-carbamate A solution of 0.11 g (0.10 mmol) of 13-[N-Boc-N,O-(2,4-dimethoxybenzylidene)-β-isobutylisoserinoyl]-7-TES-14β-amino-baccatin III in 3 ml of dichloromethane is added with 0.04 g (0.20 mmol) of $BOC_2O$, 0.03 mL (0.21 mmol) of triethylamine and 0.006 g (0.05 mmol) of dimethylaminopyridine, at room temperature. After 3 hours the reaction is quenched by addition of 4 ml of a $NH_4Cl$ aqueous saturated solution and extracted three times with 6 ml of dichloromethane. The organic phases are dried, filtered, and evaporated under reduced pressure. Chromatography ($SiO_2$, n-hexane/EtOAc/$CHCl_3$, 8.0:3.0:5.0) affords 0.09 g (0.06 mmol, 69%) of the title product. IR (KBr, cm$^{-1}$): 3450, 2961, 1803, 1733, 1370, 1239, 1089; $^1$H-NMR ($CDCl_3$, 400 MHz) relevant resonances at δ=0.59 (m, 6H, $3CH_2$), 0.94 (m, 9H, 3Me), 1.37 (s, 9H), 1.72 (s, 3H, Me), 2.19 (s, 3H, Me), 2.23 (s, 3H, Me), 2.46 (s, 3H, Me), 2.52 (m, 1H, Hα-6), 3.82 (s, 3H, OMe), 3.88 (s, 3H, OMe), 4.18 (d, 1H, H-20, J=8 Hz), 4.24 (d, 1H, H-20, J=8 Hz), 4.56 (m, 3H), 4.76 (d, 1H, J=7.2 Hz), 4.93 (d, 1H, H-5), 6.01 (d, 1H, H-2, J=7.2 Hz), 6.36 (s, 1H, H-10), 6.42 (d, 1H), 6.47-6.51 (m, 3H), 7.32-7.42 (m, 2H, arom), 7.51-7.58 (m 1H, arom), 7.92-7.98 (d, 2H, arom); $^{13}$C-NMR ($CDCl_3$, 100 MHz) relevant resonances: 5.7, 7.2, 10.7, 15.5, 21.2, 22.2, 22.4, 22.9, 23.7, 26.7, 28.1, 28.6, 37.4, 42.1, 43.7, 46.3, 55.5, 55.7, 58.7, 59.8, 71.3, 72.1, 74.1, 74.7, 76.2, 80.2, 84.4, 84.8, 104.5, 128.5, 129.0, 129.9, 133.9, 134.1, 139.5, 150.4, 151.2, 159.2, 164.6, 171.0, 200.7; Anal. Calc. $C_{64}H_{94}N_2O_{19}Si$: C, 62.8; H, 7.74. Found: C, 61.3; H, 6.64.

EXAMPLE 19

13-(N-Boc-β-isobutylisoserinoyl)-14β-t-butoxycarbamoyl-baccatin III 14,1-carbamate A solution of 0.08 g (0.07 mmol) of 13-[N-Boc-N,O-(2,4dimethoxybenzylidene)-β-isobutylisoserinoyl]-7-TES-4β-t-butoxycarbamoyl-baccatin III 14,1-carbamate in 2.1 ml of acetonitrile and 2.1 ml of pyridine is added, at 0° C., with 0.8 mL (0.1 mL/10 mg of substrate) of hydrofluoric acid-pyridine. After half an hour temperature is brought to 25° C. After three hours, the reaction is quenched by addition of 6 ml of a $NH_4Cl$ aqueous saturated solution and extracted three times with 7 ml of AcOEt. The organic phases are washed three times with a $CuSO_4$ aqueous saturated solution, dried, filtered, and evaporated under reduced pressure. The resulting reaction crude is dissolved in 3 ml of dichloromethane, then added with 0.82 ml of a 0.1 M solution of acetyl chloride in MeOH, at 0° C. After three hours the reaction is quenched by addition of 7 ml of a $NH_4Cl$ aqueous saturated solution and extracted with 8 ml of AcOEt. The organic phases are dried, filtered, and evaporated under reduced pressure. Chromatography of the resulting mixture ($SiO_2$, n-hexane/EtOAc, 1.0:1.2) yields 0.03 g (0.06 mmol, 46%) of the title product. IR (KBr, cm$^{-1}$): 3450, 2961, 1803, 1733, 1506, 1370, 1239, 1089, 732; $^1$H-NMR ($CDCl_3$, 400 MHz) relevant resonances at δ=0.98 (m, 6H, 2Me), 1.28 (s, 3H, Me), 1.31(s, 3H, Me), 1.38 (s, 9H, 3Me), 1.43 (s, 9H, 3Me), 1.66 (m, 1H, H-5'), 1.72 (s, 3H, Me), 1.91 (m, 4H, Hβ-6, Me), 2.25 (s, 3H, Me), 2.53 (m, 4H, Me, Hα-6), 3.82 (d, 1H, H-3, J=7.2 Hz), 3.95 (b, 1H, OH), 4.07 (m, 1H, H-3'), 4.25 (m, 3H, 2H-20, H-2'), 4.42 (m, H, H-7), 4.74 (d, 1H, H-14, J=7.6 Hz), 4.89 (d, 1H, N—H, J=8.8 Hz), 4.96 (m, 1H, H-5, $J_2$=7.6 Hz), 6.01 (d, 1H, H-2, J=7.2 Hz), 6.26 (m, 2H, H-10, H-13), 7.38-7.42 (m, 2H, arom), 7.54-7.58 (m 1H, arom), 7.95-7.97 (d, 2H, arom); $^{13}$C-NMR ($CDCl_3$, 100 MHz): 10.2, 16.0, 21.2, 22.6, 23.3, 23.5, 25.3, 27.0, 28.1, 28.7, 35.9, 42.0, 45.2, 51.6, 58.9, 59.5, 71.2, 72.1, 74.2, 75.3, 76.3, 80.7, 84.6, 85.4, 128.4, 129.0, 129.9, 133.3, 134.0, 141.4, 150.2, 155.9, 164.4, 169.5, 171.0, 171.2, 172.1, 202.5; Anal. Calc. $C_{48}H_{68}N_2O_{17}$: C, 61.00; H, 7.25. Found: C, 61.3; H, 6.64.

EXAMPLE 20

13-[N-Boc-N,O-(2,4-dimethoxybenzylidene)-β-isobutylisoserinoyl]-7-TES-14β-amino-baccatin III 14,1-thiocarbamate A solution of 0.171 g (0.15 mmol) of 13-[N-Boc-N,O-(2,4-dimethoxybenzylidene)-β-isobutylisoserinoyl]-7-TES-14β-amino-baccatin III in 7 ml of acetonitrile is added, at room temperature, with 0.14 g (0.61 mmol) of di-2-pyridyl-thionocarbonate. After two hours, the reaction mixture is quenched by addition of 4 ml of water and extracted three times with 6 ml of dichloromethane. The organic phases are dried, filtered, and evaporated under reduced pressure. Chromatography of the residue ($SiO_2$, n-hexane/EtOAc/$CH_2Cl_2$, 7.0:5.0:8.0) affords 0.13 g (0.11 mmol, 69%) of the title product. IR (KBr, cm$^{-1}$): 3446, 2958, 1732, 1694, 1595, 1278, 1167; $^1$H-NMR (CDCl$_3$, 400 MHz, 55° C.) relevant resonances at: δ=0.60 (m, 6H, 2CH$_2$), 0.95 (m, 9H, 3Me), 1.08 (m, 6H), 1.18-1.48 (m, 18H), 1.73 (s, 3H, Me), 2.13 (s, 3H, Me), 2.19 (s, 3H, Me), 2.23 (s, 3H, Me), 2.51 (m, 1H, Hα-6, J$_1$=6.6 Hz, J$_2$=9.7 Hz, J$_3$=14.3 Hz), 3.78 (d, 1H, H-14, J$_1$=7.4 Hz), 3.82 (s, 3H, OMe), 3.87 (s, 3H, OMe), 4.23-4.29 (m, 3H, H-3, 2H-20, J=7.2 Hz), 4.44 (m, 2H, H-7, H-3'), 4.90 (m, 1H, H-5, J=9.8 Hz), 6.09 (d, 1H, H-13, J=7.1 Hz), 6.13 (d, 1H, H-2, J=7.2 Hz), 6.48 (m, 4H, arom), 7.37-7.41 (m, 2H, arom), 7.54-7.57 (m 1H, arom), 7.96-7.98 (d, 2H, arom); $^{13}$C-NMR (CDCl$_3$, 100 MHz): 5.69, 7.17, 10.7, 15.0, 21.1, 22.3, 22.6, 22.8, 25.7, 26.2, 28.5, 37.3, 42.7, 46.4, 55.6, 55.7, 58.8, 62.8, 70.6, 72.1, 74.6, 75.7, 76.2, 80.7, 84.3, 86.9, 98.7, 104.3, 128.8, 128.8, 129.1, 129.9, 133.8, 134.7, 137.9, 159.0, 161.6, 164.8, 169.2, 169.9, 171.5, 187.9, 200.4; Anal. Calc. C$_{60}$H$_{84}$N$_2$O$_{17}$SSi: C, 61.83; H, 7.26. Found: C, 61.2; H, 7.3.

EXAMPLE 21

13-(N-Boc-β-isobutylisoserinoyl)-14β-amino-baccatin III 14,1-thiocarbamate

A solution of 0.11 g (0.10 mmol) of 13-[N-Boc-N,O-(2,4-dimethoxybenzylidene)-β-isobutylisoserinoyl]-7-TES-14β-amino-baccatin III 14,1-thiocarbamate in 2.7 ml of acetonitrile and 2.7 ml of pyridine is added, at 0° C., with 1.1 mL hydrofluoric acid-pyridine. After half an hour temperature is raised to 25° C. After two hours, the reaction is quenched by addition of 6 ml of a NH$_4$Cl aqueous saturated solution and extracted three times with 11 ml of AcOEt. The organic phases are washed three times with a CuSO$_4$ aqueous saturated solution, dried, filtered, and evaporated under reduced pressure. The resulting reaction crude (dissolved in 4 ml of dichloromethane) is added, at 0° C., with 1.2 ml of a 0.1 M solution of acetyl chloride in MeOH. After three hours the reaction is quenched by addition of 7 ml of a NH$_4$Cl aqueous saturated solution and extracted with 8 ml of AcOEt. The organic phases are dried, filtered, and evaporated under reduced pressure. Chromatography of the residue (SiO$_2$, EtOAc/n-hexane, 1.4:1) yields 0.03 g (0.05 mmol, 62%) of the title product. IR (KBr, cm$^{-1}$): 3343, 2960, 1735, 1686, 1514, 1239, 1088, 733; $^1$H-NMR (CDCl$_3$, 400 MHz): δ=0.99 (m, 6H, 2Me), 1.29 (s, 3H, Me), 1.41(s, 9H, 3Me), 1.73 (s, 3H, Me), 1.74-1.94 (m, 10H, Hβ-6, H-5', H-4', 2Me), 2.24 (s, 3H, Me), 2.31 (s, 3H, Me), 2.48 (m, 1H, Hα-6, J$_1$=6.4 Hz, J$_2$=9.0 Hz, J$_3$=15.0 Hz), 3.72 (d, 1H, H-3, J=7.2 Hz), 4.10-4.18 (m, 2H, H-2', H3'), 4.28 (m, 2H, H-20), 4.36 (m, 2H, H-7, H-20), 4.78 (d, 1H, N'—H, J=9.2 Hz), 4.94 (m, 1H, H-5, J$_1$=2.4 Hz, J$_2$=9.6 Hz), 6.09 (d, 2H, H-2, H-13, J=7.6 Hz), 6.26 (s, 1H, H-10), 7.40-7.45 (m, 2H, arom), 7.49-7.52 (m 1H, arom), 7.99-8.01 (d, 2H, arom), 9.33 (s, 1H, NH); $^{13}$C-NMR (CDCl$_3$, 100 MHz): 10.2, 15.3, 21.2, 21.9, 23.1, 23.7, 25.0, 26.2, 28.7, 35.9, 41.6, 42.7, 45.3, 52.0, 58.9, 62.0, 70.7, 72.0, 72.8, 75.3, 76.4, 76.7, 81.2, 82.1, 84.4, 94.8, 128.8, 129.8, 130.0, 133.9, 134.1, 139.9, 156.2, 164.8, 169.5, 171.0, 173.5, 202.3; Anal. Calc. C$_{44}$H$_{58}$N$_2$O$_{15}$S: C, 59.58; H, 6.59. Found: C, 61.3; H, 6.64.

EXAMPLE 22

7-TES-14-(Boc)-triazenyl-13-ketobaccatin III (0.06 g, 0.52 mmol), of potassium tert-butoxide are suspended at −75° C., under nitrogen stream and strong stirring, in 1.5 mL of anhydrous THF. After 10 minutes a solution of 0.13 g (0.19 mmol) of 7-TES-13-ketobaccatin III in 1.0 ml of THF and 0.7 ml of DMPU is added in 3 minutes at the same temperature. After 15 min, 0.06 g (0.41 mmol) of terBocazide dissolved in 1 ml of THF is added in two minutes at −70° C. After two hours, and after temperature has raised to −50° C., the reaction is quenched by addition of 5.0 ml of a NH$_4$Cl saturated aqueous solution. Temperature is slowly raised to 20° C. and the reaction mixture is diluted with 3.0 ml of Et$_2$O and extracted with 6.0 ml of a NH$_4$Cl aqueous saturated solution. The organic phases are washed three times with water, dried, filtered and evaporated under reduced pressure. Chromatography of the residue (SiO$_2$, n-hexane/EtOAc, 2.3:1.0) affords 0.022 g (0.26 mmol, 50%) of the title product. IR (KBr, cm$^{-1}$): 3500-3100, 2962, 1731, 1374, 1238; $^1$H-NMR (CDCl$_3$, 400 MHz): $^1$H-NMR (CDCl$_3$, 400 MHz): relevant resonances δ=0.58 (m, 6H, 3CH$_2$), 0.91 (m, 9H, 3Me), 1.11 (s, 3H, Me), 1.31 (s, 3H, Me), 1.55 (s, 9H, 3Me), 1.71 (s, 3H, Me), 1.88 (m, 1H, Hβ-6), 2.20 (s, 3H, Me), 2.21 (s, 3H, Me), 2.22 (s, 3H, Me), 2.52 (m, 1H, Hα-6), 3.91 (d, 1H, H-3), 4.23 (s, 2H, 2H-20), 4.47 (m, 2H, H-7, H-14), 4.92 (d, 1H, H-5), 5.80 (d, 1H, CH$_2$), 6.54 (s, 1H, H-10), 6.89 (S, 1H), 7.38-7.60 (m, 4H, arom), 7.96-7.99 (m, 2H, arom); $^{13}$C-NMR (CDCl$_3$, 100 MHz): δ=5.5, 7.0, 10.0, 14.3, 19.2, 21.0, 22.0, 28.3, 33.8, 37.3, 43.1, 45.1, 59.3, 72.5, 73.5, 73.9, 75.6, 76.4, 76.7, 80.8, 83.3, 84.0, 128.9, 129.0, 129.2, 130.3, 130.4, 133.7, 138.6, 150.4, 152.1, 165.7, 169.2, 171.0, 194.7, 200.3; MS (mz) (M$^+$ calc. C$_{42}$H$_{59}$N$_3$O$_{13}$Si 841.4), 842.4, 714, 652, 574; Anal. Calc. C$_{42}$H$_{59}$N$_3$O$_{13}$Si: C, 59.91; H, 7.06. Found: C, 58.9; H, 6.57.

EXAMPLE 23

14-[N,N'-bis-(benzyloxycarbonyl)hydrazino]-7-Boc-13-ketobaccatin III 0.16 g (1.47 mmol) of potassium tert-butoxide are suspended, under nitrogen stream and strong stirring, in 3.0 ml of anhydrous THF at −72° C. The mixture is added, in two minutes and at the same temperature, with 0.37 g (0.54 mmol) of 7-Boc-13-ketobaccatin III in 2.5 ml of THF and 1.8 ml of DMPU. After 15 minutes, 0.32 g (1.19 mmol) di-tert-benzyl-azodicarboxylate dissolved in 3.0 ml of THF and 0.2 ml of DMPU are slowly added at −68° C. Temperature is raised −50° C., and after 8 hours the reaction mixture is quenched by addition of 2 mL (0.03 mmol) of acetic acid diluted with 10 ml of ethyl ether and extracted with 10 ml of a NH$_4$Cl aqueous saturated solution. The organic phases are washed three times with water, dried, filtered and evaporated under reduced pressure. Chromatography of the residue (SiO$_2$, n-hexane/EtOAc, 1.3:5.0) affords 0.30 g (0.29 mmol, 55%) of the title product. $^1$H-NMR (CDCl$_3$, 400 MHz): δ=0.86 (s, 3H, Me), 1.23 (s, 3H, Me), 1.47 (s, 9H, 3Me), 1.82 (s, 3H, Me), 1.97 (m, 1H, Hβ-6, J$_1$=2.5 Hz, J$_2$=10.9 Hz, J$_3$=14.3 Hz), 2.13 (s, 3H, Me), 2.18 (s, 3H, Me), 2.19 (s, 3H, Me), 2.59 (m, 1H, Hα-6, J$_1$=7.2 Hz, J$_2$=9.5 Hz, J$_3$=14.3 Hz), 4.14 (d, 1H, H-3, 6.2 Hz), 4.24 (d, 1H, H-20, J=8.6 Hz), 4.37 (d, 1H, H-20, J=8.6 Hz), 4.90 (s, 1H, H-14), 4.92 (d, 1H, H-5, J$_1$=2.5 Hz, J$_2$=9.5 Hz), 4.99 (d, 1H, CH$_2$, J=12.5 Hz), 5.06 (d, 1H, CH$_2$, J=12.5 Hz), 5.12 (d, 1H, CH$_2$, J=12.5 Hz), 5.18 (d, 1H, CH$_2$, J=12.5 Hz), 5.41 (m, 1H, H-7, J$_1$=10.8 Hz, J$_2$=6.9 Hz), 5.62 (s, 1H), 5.97 (d, 1H, H-2, J=6.2 Hz), 6.56 (s, 1H, H-10), 6.89 (s, 1H), 7.15-7.30 (m, 10H, arom), 7.34-7.40 (m, 2H, arom), 7.50-7.55 (m 1H, arom), 8.25 (d, 2H, arom); $^{13}$C-NMR (CDCl$_3$, 100 MHz): δ=10.9, 14.4, 20.1, 21.0, 22.0, 27.9, 33.6, 43.5, 45.9, 57.2, 66.1, 68.8, 69.5, 73.6, 74.4, 75.2, 75.8, 76.8, 80.9, 83.3, 84.2, 127.5, 128.3, 128.5, 128.6, 128.7, 128.8, 128.9, 129.2, 131.1, 133.6, 135.0, 135.3, 138.4, 152.6, 153.3, 157.0, 158.0, 166.2, 168.4, 171.7, 196.4, 200.2; Anal. Calc. C$_{52}$H$_{58}$N$_2$O$_{17}$: C, 63.53; H, 5.95. Found: C, 62.5; H, 6.02.

EXAMPLE 24

14-[N,N'-bis-(Boc)hydrazino]-7-Boc-13-ketobaccatin III 0.16 g of potassium tert-butoxide (1.47 mmol) are suspended, under nitrogen stream and strong stirring, in 3.0 ml of anhydrous THF at −72° C. The mixture is added, in two minutes and at the same temperature, with 0.37 g (0.54 mmol) of 7-Boc-13-ketobaccatin III in 2.5 ml of THF and 1.8 ml of DMPU. After 15 minutes, 0.27 g (1.19 mmol) di-tert-butyl azodicarboxylate dissolved in 3.0 ml of TMF and 0.2 ml of DMPU are slowly added at −68° C. After 1 hour the reaction is quenched by addition of 2 mL (0.03 mmol) of acetic acid diluted with 10 ml of ethyl ether and extracted with a $NH_4Cl$ aqueous saturated solution. The organic phases are washed three times with water, dried, filtered and evaporated under reduced pressure. Chromatography of the residue ($SiO_2$, n-hexane/EtOAc, 1.3:5.0) affords 0.35 g (0.37 mmol, 70%) of the title product. $^1$H-NMR ($CDCl_3$, 400 MHz): δ=1.00 (s, 3H, Me), 1.26 (s, 3H, Me), 1.35 (s, 9H, 3Me), 1.40 (s, 9H, 3Me), 1.46 (s, 9H, 3Me), 1.82 (s, 3H, Me), 1.97 (m, 1H, Hβ-6, $J_1$=2.6 Hz, $J_2$=10.7 Hz, $J_3$=14.3 Hz), 2.17 (s, 3H, Me), 2.18 (s, 3H, Me), 2.21 (s, 3H, Me), 2.59 (m, 1H, Hα-6, $J_1$=7.0 Hz, $J_2$=9.7 Hz, $J_3$=14.3 Hz), 4.15 (d, 1H, H-3, 6.3 Hz), 4.23 (d, 1H, H-20, J=8.4 Hz), 4.35 (d, 1H, H-20, J=8.4 Hz), 4.90 (d, 1H, H-5, $J_1$=2.2 Hz, $J_2$=9.7 Hz), 5.14 (s, 1H, H-14), 5.41 (m, 1H, H-7, $J_1$=10.7 Hz, $J_2$=6.9 Hz), 5.58 (s, 1H), 5.97 (d, 1H, H-2, J=6.4 Hz), 6.53 (s, 1H, H-10), 6.58 (s, 1H), 7.38-7.42 (m, 2H, arom), 7.50-7.55 (m 1H, arom), 8.29 (d, 2H, arom); $^{13}$C-NMR ($CDCl_3$, 100 MHz): δ=10.9, 14.3, 20.1, 21.0, 21.9, 27.9, 28.1, 28.2, 33.7, 34.6, 43.6, 45.9, 57.3, 65.1, 73.4, 74.5, 75.0, 76.1, 76.8, 80.9, 82.7, 83.2, 83.3, 84.2, 128.4, 129.4, 131.2, 133.3, 138.5, 152.6, 153.2, 155.8, 157.3, 166.2, 168.4, 171.7, 196.9, 200.4; Anal. Calc. $C_{46}H_{62}N_2O_{19}$: C, 58.34; H, 6.60. Found: C, 60.3; H, 6.64.

EXAMPLE 25

13-Ketobaccatin III 13,14-triisopropylsilyl enolether

A solution of 0.07 g (0.10 mmol) of 7-TES-13-ketobaccatin III in 2 ml of anhydrous THF is added with 0.25 mL (0.25 mmol) of a potassium tert-butoxide solution 1.0 M solution, under stirring and nitrogen stream, at −75° C. After 12 minutes, 0.04 mL (0.17 mmol) of triisopropylsilyl chloride is added very slowly with a syringe at the same temperature. After 45 minutes, the reaction is quenched by addition of 7 ml of a $NH_4Cl$ aqueous saturated solution and extracted three times with 15.0 ml of $Et_2O$. The organic phases are washed four times with water, dried, filtered and evaporated under reduced pressure. Chromatography of the residue ($SiO_2$, n-hexane/EtOAc/$Et_{20}$, 1.8:0.7:0.5) affords 0.035 g (0.04 mmol, 43%) of the title compound. IR (KBr, $cm^{-1}$): 3474, 2948, 1725, 1369, 1239, 1108, 732; $^1$H-NMR ($CDCl_3$, 400 MHz): δ=0.58 (m, 6H, 3$CH_2$), 0.92 (m, 9H, 3Me), 1.05 (s, 3H, Me), 1.14 (m, 18H, 6Me), 1.25 (s, 3H, Me), 1.70 (s, 3H, Me), 1.88 (m, 1H, Hβ-6, $J_1$=1.2 Hz, $J_2$=11.2 Hz, $J_3$=14 Hz), 2.10 (s, 3H, Me), 2.19 (m, 3H, Me), 2.23 (s, 3H, Me), 2.50 (m, 1H, Hα-6, $J_1$=1.2Hz, $J_2$=9.5 Hz, $J_3$=14.0 Hz), 3.74 (d, 1H, H-3, J=7.6 Hz), 4.16 (d, 1H, H-20, J=8.4 Hz), 4.27 (d, 1H, H-20, J=8.4 Hz), 4.46 (m, 1H, H-7, $J_1$=6.4 Hz, $J_2$=11.2 Hz), 4.82 (s, 1H, H-14), 4.94 (d, 1H, H-5, $J_1$=1.2 Hz, $J_2$=8 Hz), 5.76 (d, 1H, H-2, J=7.2 Hz), 6.40 (s, 1H, H-10), 7.43-7.47 (m, 2H, arom), 7.57-7.60 (m 1H, arom), 8.07-8.09 (d, 2H, arom); $^{13}$C-NMR ($CDCl_3$, 100 MHz): δ=5.71, 7.2, 10.7, 13.0, 14.2, 18.1, 18.4, 18.5, 19.8, 21.4, 22.3, 28.5, 30.1, 37.5, 41.0, 45.6, 58.4, 72.2, 74.2, 76.2, 75.5, 80.8, 81.9, 84.4, 110.6, 128.7, 129.7, 130.2, 133.6, 134.7, 137.8, 153.5, 166.7, 169.3, 170.0, 201.7. MS (mz) (M+calc. $C_{47}H_{72}O_{10}Si_2$ 854.5), 855.5, 795.5, 735.5, 673.4; Anal. Calc. $C_{47}H_{72}O_{10}Si_2$: C, 66.16; H, 8.51. Found: C, 67.5; H, 8.64.

EXAMPLE 26

7-TES-13-ketobaccatin III 13,14-diethylphosphoenolate

A solution of 7-TES-13-ketobaccatin III (258 mg, M.W.=698 g/mol, 0.37 mmol) in anhydrous THF (7.5 ml) is added drop by drop with a 0.5M solution of KHMDS (1.7 ml, 0.85 mmol, 2.3 eq.) in toluene, under nitrogen and at −78° C. After stirring at −78° C. for 1 hour, diethylchlorophosphosfate (80 μl, M.W.=172.55 g/mol, 0.55 mmol, 1.2 g/ml, 1.5 eq.) is added thereto. The mixture is left under stirring at −78° C. for 30 minutes, at 0° C. for 1.5 hours and at room temperature overnight, then added with water (15 ml) and extracted with AcOEt (3×15 ml). The crude (300 mg) is purified by flash silica gel chromatography (AcOEt:hexane 1:1) to obtain the desired product (150 mg, M.W.=834 g/mol, 0.18 mmol) in a 48% yield. TLC (AcOEt:hexane 1:1) $R_f$=0.26

EXAMPLE 27

7-Boc-13-ketobaccatin III 13,14-Boc-enol ester

A solution of 13-ketobaccatin III (0.525 g, 0.9 mmol) and DMAP (9 mg, 70 mmol) in methylene chloride (5.0 mL) is added with Boc anhydride (0.236 g, 1.10 mmol) under stirring. The solution is left under stirring at room temperature overnight. The solvent is removed under reduced pressure and the oily residue is dissolved in 50% aqueous acetone (10 mL) and left under stirring for 1 hour. The solution is extracted with methylene chloride and the combined organic phases are dried over sodium sulfate and then evaporated. The residue is chromatographed on silica to give 0.36 g of the title product (0.52 mmol, 58%), 80 mg of unreacted product and 50 mg of 7-Boc-13-ketobaccatin III.

$[α]_D^{20}$=−35.6° (c 1.05, $CHCl_3$); IR ($CDCl_3$, $cm^{-1}$): 3483, 1731, 1676, 1371, 1274; $^1$H-NMR ($CDCl_3$, 400 MHz): δ=1.20 (s, 3H, Me), 1.22 (s, 3H, Me), 1.47 (s, 9H, 3Me), 1.76 (s, 3H, Me), 1.91 (m, 1H, H?-6, $J_1$=10.4 Hz, $J_2$=14.8 Hz, $J_3$=2.0 Hz), 1.92 (b, 1H, OH), 2.17 (s, 3H, Me), 2.19 (s, 3H, Me), 2.20 (s, 3H, Me), 2.64 (m, 1H, H?-6, $J_1$=7.2 Hz, $J_2$=14.8 Hz, $J_3$=9.5 Hz), 2.66 (d, 1H, H-14, J=19.6 Hz), 2.94 (d, 1H, H-14, J=19.6 Hz), 4.02 (d, 1H, H-3, J=6.8 Hz), 4.09 (d, 1H, H-20, J=9.0 Hz), 4.32 (d, 1H, H-20, J=9.0 Hz), 4.94 (d, 1H, H-5, $J_1$=9.5 Hz, $J_2$=2.0 Hz), 5.39 (m, 1H, H-7, $J_1$=10.4 Hz, $J_2$=7.2 Hz), 5.67 (d, 1H, H-2, J=6.8 Hz), 6.57 (s, 1H, H-10), 7.44-7.50 (m, 2H, arom), 7.61-7.64 (m 1H, arom), 8.30 (d, 2H, arom); $^{13}$C-NMR ($CDCl_3$, 100 MHz): δ=10.7, 14.0, 18.4, 21.0, 21.9, 27.9, 33.1, 33.6, 42.7, 46.7, 57.3, 72.8, 74.7, 76.3, 76.5, 77.4, 78.7, 80.5, 83.4, 84.0, 128.9, 129.0, 130.3, 134.3, 141.0, 152.4, 152.5, 167.0, 168.3, 170.3, 198.4, 200.5. Anal. Calcd for $C_{36}H_{44}O_{13}$: C, 63.15; H, 6.48. Found: C, 63.39; H, 6.60.

EXAMPLE 28

7-TES-13-keto-14-(N,N'-bis-(benzyloxycarbonyl) hydrazino)-baccatin III

A solution of 13-keto-7-TES-baccatin III (450 mg, 0.64 mmol) in anhydrous THF (12 mL) and DMPU (2.5 mL) under stirring is cooled to −70° C. under nitrogen, then added drop by drop with potassium tert-butoxide (1.61 mL, 1M in THF, 1.61 mmol). The solution is stirred at −65° C. for 45 minutes, then added with dibenzylazadicarboxylate (276 mg, 90%, 0.82 mmol), checking the reaction by TLC: after 2 hours the conversion is still uncompleted, therefore further dibenzylazadicarboxylate (69 mg, 0.20 mmol) is added. After 1 h the reaction is treated with acetic acid (0.15 mL, 40% in THF) and left to warm at room temperature, then diluted with a NaCl aqueous saturated solution (10 mL) and extracted with AcOEt (2×10 mL). The organic phase is washed with a NaCl aqueous saturated solution (10 mL), dried ($Na_2SO_4$) and evaporated. The residue is purified by column chromatography (silica, 1→2% AcOEt in $CH_2Cl_2$) to obtain the title product (451 mg, 70%) and 13-keto-7-TES-baccatin III (45 mg, 10%). $R_f$=0.6 (silica, 50% AcOEt in cyclohexane); m.p. 181-182° C. ($Et_2O$/EtP); $^1$H-NMR (200 MHz, $CDCl_3$) δ 8.29 (d, J=7.0 Hz, 2H, Bz), 7.19-7.55 (m, 13H, Bz, Ar), 6.87 (s, 1H, NH), 6.53 (s, 1H, 10-H), 5.99 (d, J=6.6 Hz, 1H, 2-H), 5.63 (s, 1H, 14-H), 5.16 (d, J=3.3 Hz, 2H, $CH_2Ph$), 5.04 (d, J=4.8 Hz, 2H, $CH_2Ph$), 4.88 (d, J=4.0 Hz, 1H, 5-H), 4.51 (dd, J=6.6, 4.0 Hz, 1H, 7-H), 4.32 (Abq, 2H, 20-H), 4.01 (d, J=6.6 Hz, 1H, 3-H), 2.42-2.61 (m, 1H, 6-H), 2.23 (s, 3H, 4-OAc), 2.22 (s, 3H, 10-OAc), 2.15 (s, 3H; 18-Me), 1.84-1.98 (m, 1H, 6-H), 1.74 (s, 3H, 19-Me), 1.29 (s, 3H, 16-Me), 1.28 (s, 3H, 17-Me), 0.90-0.98 (t, J=8.7 Hz, 9H, $Si(CH_2CH_3)_3$), 0.58-0.66 (m, 6H, $Si(CH_2CH_3)_3$); $^{13}$C-NMR (300 MHz, $CDCl_3$) δ 200.1, 196.7, 171.9, 169.3, 166.3, 158.1, 157.1, 138.0, 135.5, 135.2, 133.6, 131.3, 129.5, 129.0, 128.9, 128.7, 128.5, 127.7, 84.6, 81.3, 75.8, 75.3, 74.0, 72.5, 69.6, 68.9, 66.3, 59.6, 46.0, 43.7, 37.6, 34.8, 22.2, 21.1, 20.2, 14.2, 10.2, 7.1, 5.6.

EXAMPLE 29

7-TES-13-keto-14-hydrazino-baccatin III

A solution of 13-keto-7-TES-14-(N,N'-bis-(benzyloxycarbonyl)-hydrazino)-baccatin (564 mg, 0.55 mmol) in AcOEt (45 mL) is hydrogenated with 10% Pd/C as catalyst (557 mg) for 45 minutes. The catalyst is filtered off through Celite, then the solvent is evaporated off under reduced pressure without heating to obtain the title product (386 mg, 96%). This compound is unstable in various conditions (chromatographic column) and solvents ($CDCl_3$). $R_f$=0.2 (silica, 5% AcOEt in $CH_2Cl_2$); $^1$H-NMR (200 MHz, $CDCl_3$) δ 8.21 (d, J=7.3 Hz, 2H, Bz), 7.41-7.61 (m, 3H, Bz), 6.54 (s, 1H, 10-H), 5.85 (d, J=6.6 Hz, 1H, 2-H), 5.37 (s, 1H), 5.18 (s, 1H), 4.92 (d, J=8.1 Hz, 1H, H-5), 4.51 (dd, J=6.6, 4.1 Hz, 1H, H-7), 4.29 (s, 2H, H-20), 3.92 (d, J=7.0 Hz, 1H, H-3), 2.47-2.62 (m, 1H, H-6), 2.25 (s, 3H, 4-OAc), 2.23 (s, 3H, 10-OAc), 2.06 (s, 3H; 18-Me), 1.84-1.98 (m, 1H, 6-H), 1.74 (s, 3H, 19-Me), 1.31 (s, 3H, 16-Me), 1.28 (s, 3H, 17-Me), 0.90-0.98 (t, J=8.7 Hz, 9H, $Si(CH_2CH_3)_3$), 0.58-0.66 (m, 6H, $Si(CH_2CH_3)_3$).

EXAMPLE 30

7-TES-13-keto-baccatin III [14,1-d]-3,4-dehydrofuran-2-one

A solution of 13-keto-7-TES-baccatin (600 mg, 0.86 mmol) in anhydrous THF (20 mL) under stirring is cooled to −70° C. under nitrogen, then added drop by drop with potassium tert-butoxide (2.16 mL, 1M in THF, 2.16 mmol) and stirred at −65° C. for 45 minutes. Ethyl glyoxylate (0.36 mL, 50% in toluene, 1.29 mmol) is then added checking the reaction by TLC: after 2 hours the conversion is still uncompleted, therefore further dibenzylazadicarboxylate (0.12 mL, 0.43 mmol) is added. After 1 h the reaction is treated with anhydrous citric acid (290 mg) and left to warm at room temperature, then immediately purified by column chromatography (silica, 10→20% AcOEt in cyclohexane) to obtain the title product (503 mg, 79%) as a yellow solid. $R_f$=0.55 (silica, 50% AcOEt in cyclohexane); m.p. 252-253° C. ($Et_2O$/Etp); $^1$H-NMR (200 MHz, $CDCl_3$) δ 7.97 (d, J=8.4 Hz, 2H, Bz), 7.43-7.62 (m, 3H, Bz), 6.87 (s, 1H, 21-H), 6.66 (s, 1H, 10-H), 6.16 (d, J=6.9 Hz, 1H, 2-H), 4.88 (d, J=8.8 Hz, 1H, 5-H), 4.50 (dd, J=6.6, 3.6 Hz, 1H, 7-H), 4.13-4.24 (Abq, 2H, 20-H), 3.98 (d, J=6.9 Hz, 1H, 3-H), 2.49-2.64 (m, 1H, 6-H), 2.39 (s, 3H, 4-OAc), 2.27 (s, 3H, 10-OAc), 2.14 (s, 3H; 18-Me), 1.84-1.98 (m, 1H, 6-H), 1.75 (s, 3H, 19-Me), 1.45 (s, 3H, 16-Me), 1.27 (s, 3H, 17-Me), 0.91-0.99 (t, J=8.4 Hz, 9H, $Si(CH_2CH_3)_3$), 0.56-0.68 (m, 6H, $Si(CH_2CH_3)_3$); $^{13}$C (300 MHz, $CDCl_3$) δ 199.4, 182.9, 171.0, 169.5, 165.2, 158.7, 156.3, 143.1, 134.7, 130.5, 129.4, 128.7, 127.4, 94.3, 84.4, 77.3, 77.1, 76.4, 72.8, 68.6, 60.8, 47.3, 45.2, 32.9, 22.3, 21.4, 20.8, 14.6, 10.3, 7.4, 5.3; $[\alpha]^{20}_D$+72 (c 1, $CHCl_3$).

EXAMPLE 31

7-TES-13,14-dehydro-baccatin III [14,1-d]-furan-2-one

A solution of 13-keto-7-TES-baccatin [14,1-d]-3,4-dehydrofuran-2-one derivative (90 mg, 0.12 mmol) in AcOEt (10 mL) is hydrogenated with 10% Pd/C as the catalyst (90 mg) for 45 minutes. The catalyst is filtered off through Celite, then the solvent is evaporated off and the residue is purified through a column (silica, 20→50% AcOEt in cyclohexane) to obtain the title product (67 mg, 75%) as a white solid. $R_f$=0.2 (silica, 50% AcOEt in cyclohexane); m.p. 235-236° C. (EtOAc/hexane); $^1$H-NMR (200 MHz, $CDCl_3$) δ8.01 (d, J=6.9 Hz, 2H, Bz), 7.44-7.62 (m, 3H, Bz), 6.43 (s, 1H, 10-H), 6.10 (d, J=6.6 Hz, 1H, 2-H), 4.98 (d, J=5.9 Hz, 1H, 5-H), 4.44 (dd, J=6.6, 3.6 Hz, 1H, 7-H), 4.17-4.39 (Abq, 2H, 20-H), 3.76 (d, J=7.0 Hz, 1H, 3-H), 3.13-3.41 (Abq, 2H, 21-H), 2.49-2.64 (m, 1H, 6-H), 2.23 (s, 3H, 4-OAc), 2.22 (s, 3H, 10-OAc), 2.20 (s, 3H; 18-Me), 1.84-1.98 (m, 1H, 6-H), 1.74 (s, 3H, 19-Me), 1.27 (s, 3H, 16-Me), 1.16 (s, 3H, 17-Me), 0.90-0.98 (t, J=8.1 Hz, 9H, $Si(CH_2CH_3)_3$), 0.56-0.68 (m, 6H, $Si(CH_2CH_3)_3$); $^{13}$C (300 MHz, $CDCl_3$) δ 201.5, 175.0, 170.1, 169.6, 164.9, 148.7, 136.8, 134.9, 133.8, 129.6, 128.8, 128.7, 102.2, 92.4, 84.1, 80.8, 76.1, 75.9, 72.2, 70.4, 58.4, 45.0, 39.6, 37.3, 32.0, 28.1, 21.3, 20.9, 19.6, 13.5, 10.0, 6.7, 5.3.

EXAMPLE 32

7-TES-baccatin [14,1-d]-3,4-dehydrofuran-2-one

A solution of $Bu_4NBH_4$ (180 mg, 0.7 mmol) in MeOH (10 mL) under stirring is cooled to −30° C., then dropped into a solution of 7-TES-13-keto-baccatin [14,1-d]-3,4-dehydrofuran-2-one (200 mg, 0.28 mmol) in THF (1 mL). After 30 minutes the reaction mixture is treated with citric acid (180 mg) and left to warm at room temperature. After addition of water (10 mL), the mixture is extracted with AcOEt (2×10 mL) and the organic phase is washed with water (5 mL), dried over $Na_2SO_4$ and evaporated. The residue is purified by silica gel chromatography (20→30% AcOEt in cyclohexane) to obtain 7-TES-13,14-dehydro-baccatin [14,1-d]-furan-2-one (103 mg, 52%) and the title product (52 mg, 26%) as white solids.

$R_f$=0.15 (silica, 50% AcOEt in cyclohexane); $^1$H-NMR (200 MHz, $CDCl_3$) δ 8.02 (d, J=6.9 Hz, 2H, Bz), 7.40-7.63 (m, 3H, Bz), 6.47 (s, 1H, 21-H), 6.25 (s, 1H, 10-H), 6.12 (d, J=8.1 Hz, 1H, 2-H), 5.14 (m, 1H, 13-H), 4.92 (d, J=8.1 Hz, 1H, 5-H), 4.55 (dd, J=7.0, 3.6 Hz, 1H, 7-H), 4.15-4.30 (Abq, 2H, 20-H), 4.07 (d, J=8.0 Hz, 1H, 3-H), 2.49-2.56 (m, 1H, 6-H), 2.28 (s, 3H, 4-OAc), 2.22 (s, 3H, 10-OAc), 2.13 (s, 3H; 18-Me), 1.84-1.97 (m, 1H, 6-H), 1.80 (s, 3H, 19-Me), 1.35 (s, 3H, 16-Me), 1.27 (s, 3H, 17-Me), 0.90-0.99 (t, J=8.1 Hz, 9H, Si($CH_2CH_3$)$_3$), 0.58-0.65 (m, 6H, Si($CH_2CH_3$)$_3$).

EXAMPLE 33

13-[N-Boc-N,O-(2,4-dimethoxybenzylidene)-β-isobutylisoserinoyl]-7-TES-baccatin [14,1-d]-3,4-dehydrofuran-2-one Preparation of N-Boc-N,O-(2,4-dimethoxybenzylidene)-β-isobutylisoserine N-Boc-N,O-(2,4-dimethoxybenzylidene)-β-isobutylisoserine sodium salt (72 mg, 0.168 mmol) is dissolved in water (5 mL) and added with $CH_2Cl_2$ (3 mL). An $NaHSO_4$ aqueous solution (2M, 0.15 mL) is dropped therein to adjust pH to 3.0. After stirring for some minutes, the organic phase is separated and the aqueous phase is extracted with $CH_2Cl_2$ (2 mL). The combined organic extracts are washed with water (5 mL) and with a NaCl saturated solution (5 mL), dried over $Na_2SO_4$ and evaporated to obtain the free acid (68 mg, 100%) as a white solid.

Esterification

7-TES-13,14-dehydro-baccatin [14,1-d]-furan-2-one (100 mg, 0.14 mmol) is suspended in toluene (4 mL) and added drop by drop with N-Boc-N,O-(2,4-dimethoxybenzylidene)-β-isobutylisoserine (68 mg, 0.168 mmol) dissolved in $CH_2Cl_2$ (2 mL), then with N,N-dimethylaminopyridine (DMAP) (7 mg) and dicyclohexylcarbodiimide (DCC) (35 mg, 0.168 mmol). The reaction mixture is heated at 70° C. for 3 hours, then left to cool and kept at room temperature until complete precipitation of DCU. The precipitate is filtered (DCU) and washed with toluene (2×3 mL), then the filtrate is washed with saturated $NaHCO_3$ (5 mL), then with 0.4 M HCl (10 mL) to remove DMAP and finally with saturated $NaHCO_3$ (5 mL). The organic phase is dried over $Na_2SO_4$ and evaporated to dryness. The residue is purified by column chromatography (20→30% AcOEt in cyclohexane) to obtain a first fraction containing the title product (88 mg, 56%). $R_f$=0.55 (silica, 20% AcOEt in cyclohexane); m.p. 150-153° C. (iPR$_2$O/EtP);1H-NMR (200 MHz, CDCl$_3$) δ 7.97 (d, J=7.0 Hz, 2H, Bz), 7.42-7.60 (m, 3H, Bz), 7.19-7.25 (m, 1H,), 6.68 (s, 1H, 10-H), 6.46-6.54 (m, 2H,), 6.03 (s, 1H,), 5.98 (d, J=5.1 Hz, 1H, 2-H), 5.81 (s, 1H,), 5.05-5.13 (m, 1H, 4.91 (d, J=7.0 Hz, 1H, 5-H), 4.42 (m, 1H, 7-H), 4.28 (s, 2H, 20-H), 3.95 (d, J=5.5 Hz, 1H, 3-H), 3.89 (s, 3H, O-Me), 3.85 (s, 3H, O-Me), 2.81 (s, 1H, 13-H), 2.49-2.64 (m, 1H, 6-H), 2.34 (s, 3H, 4-OAc), 2.22 (s, 3H, 10-OAc), 2.08 (s, 3H; 18-Me), 1.84-1.98 (m, 1H, 6-H), 1.69 (s, 3H, 19-Me), 1.27 (s, 3H, 16-Me), 1.24 (s, 3H, 17-Me), 1.03-1.13 (, 9H, N-Boc), 0.90-0.97 (t, J=7.7 Hz, 9H, Si($CH_2CH_3$)$_3$), 0.54-0.62 (m, 6H, Si($CH_2CH_3$)$_3$); $^{13}$C (300 MHz, CDCl$_3$) δ 203.5, 170.6, 170.2, 168.8, 164.5, 161.7, 159.1, 155.7, 139.0, 138.5, 133.9, 130.4, 129.6, 129.0, 128.7, 128.3, 127.7, 118.8, 104.3, 98.6, 90.4, 87.0, 84.3, 81.3, 80.8, 79.5, 75.0, 73.6, 72.9, 72.1, 67.7, 60.1, 58.9, 56.9, 55.4, 50.9, 50.1, 45.4, 43.7, 39.3, 38.3, 37.4, 29.7, 29.1, 28.2, 26.9, 25.5, 22.8, 22.6, 22.5, 21.1, 19.8, 15.9, 9.5, 6.8, 5.6; $[\alpha]^{20}_D$+44 (c 0.25, CHCl$_3$).

EXAMPLE 34

13-[N-Boc-N,O-(2,4-dimethoxybenzylidene)-β-isobutylisoserinoyl]-baccatin [14,1-d]-3,4-dehydrofuran-2-one A solution of 13-[N-Boc-N,O-(2,4-dimethoxybenzylidene)-β-isobutylisoserinoyl]-7-TES-baccatin [14,1-d]-3,4-dehydrofuran-2-one (63 mg, 0.056 mmol) in acetonitrile (3 mL) and pyridine (3 mL) is stirred in polyethylene container and cooled to 0° C. A solution of HF-pyridine (0.4 mL) is slowly added thereto, then the mixture is left to warm at room temperature and kept under stirring for 24 hours, then poured in cold water (10 mL) and extracted with $CH_2Cl_2$ (2×5 mL). The organic phase is washed with 2M $NaHSO_4$ to pH 2, then with 5% $NaHCO_3$ (5 mL) and finally with a NaCl saturated solution (5 mL). The mixture is dried over $Na_2SO_4$ and the solvent is evaporated off. The residue is purified by column chromatography (25→35% AcOEt in cyclohexane) to obtain the title product (45 mg, 80%) as a white solid. $R_f$=0.3 (silica, 50% AcOEt in cyclohexane); $^1$H-NMR (200 MHz, CDCl$_3$) δ 7.95 (d, J=7.5 Hz, 2H, Bz), 7.43-7.59 (m, 3H, Bz), 7.22-7.27 (m, p 1H,), 6.66 (s, 1H, 21-H), 6.51-6.54 (m, 2H,), 5.99 (d, J=5.5 Hz, 1H, 2-H), 5.84 (s, 1H,), 5.57 (s, 1H, 10-H), 5.05-5.13 (m, 1H,), 4.90 (d, J=7.0 Hz, 1H, 5-H), 4.70(=), 4.42 (m, 1H, 7-H), 4.30-4.32 (ABq, 2H, 20-H), 3.89 (s, 3H, O-Me), 3.86 (d, J=5.5 Hz, 1H, 3-H), 3.84 (s, 3H, O-Me), 3.03 (s, 1H, 13-H), 2.49-2.64 (m, 1H, 6-H), 2.34 (s, 3H, 4-OAc), 2.27 (s, 3H, 10-OAc), 1.88 (s, 3H; 18-Me), 1.84-1.98 (m, 1H, 6-H), 1.69 (s, 3H, 19-Me), 1.27 (s, 3H, 16-Me), 1.25 (s, 3H, 17-Me), 1.07-1.12 (9H, N-Boc). $^{13}$C (300 MHz, CDCl$_3$) δ 205.6, 172.2, 171.2, 170.1, 169.0, 164.9, 162.1, 159.4, 155.6, 153.5, 139.2, 137.6, 134.3, 130.3, 129.3, 129.1, 128.5, 127.9, 119.0, 114.2, 104.6, 98.9, 90.5, 87.2, 84.7, 81.6, 81.2, 79.8, 76.8, 72.0, 68.3, 59.2, 58.4, 57.5, 55.9, 55.8, 44.0, 39.4, 38.1, 35.8, 30.0, 29.3, 28.5, 25.8, 23.2, 22.9, 22.8, 21.3, 20.8, 16.3, 9.5; $[\alpha]^{20}_D$+82 (c 0.9, CHCl$_3$).

EXAMPLE 35

13-(N-Boc-β-isobutylisoserinoyl)-baccatin [14,1-d]-3,4-dehydrofuran-2-one

A solution of 13-[N-Boc-N,O-(2,4-dimethoxybenzylidene)-β-isobutylisoserinoyl]-baccatin [14,1-d]-3,4-dehydrofuran-2-one derivative (44 mg, 0.04 mmol) in $CH_2Cl_2$ (4 mL) under stirring is cooled to 0° C. A solution of acetyl chloride in methanol (0.01 M, 0.7 mL) is dropped into the mixture, which is left to warm at room temperature, checking the reaction by TLC: after 18 hours the starting product is still partly present, therefore a further amount of acetyl chloride solution (0.3 mL) is added. After 3 hours a $NH_4Cl$ saturated solution (4 mL) is added and the organic phase is dried over $Na_2SO_4$ and evaporated. The residue is purified by column chromatography (25→35% AcOEt in cyclohexane) to obtain the title product (30 mg, 85%) as a white solid. $R_f$=0.2 (silica, 50% AcOEt in cyclohexane); m.p. 149-154° C. ($CH_2Cl_2$/iPR$_2$O); $^1$H-NMR (200 MHz, CDCl$_3$) δ 7.95 (d, J=7.4 Hz, 2H, Bz), 7.42-7.60 (m, 3H. Bz), 6.16 (s, 1H, 21-H), 5.99 (d, J=5.5 Hz, 1H, 2-H), 5.57 (s, 1H, 10-H), 4.90 (dd, J=3.7, 6.2 Hz, 1H, 5-H), 4.77 (d, J=10.2 Hz, 1H, NH), 4.30-4.47 (m, 4H, 2'-H, 7-H, 20-H, 3'-H), 3.81 (d, J=5.5 Hz, 1H, 3-H, 3.00 (s, 1H, 13-H), 2.49-2.61 (m, 1H, 6-H), 2.45 (s, 3H, 4-OAc), 2.27 (s, 3H, 10-OAc), 1.84-1.97 (m, 1H, 6-H), 1.83 (s, 3H; 18-Me), 1.69 (s, 3H, 19-Me), 1.44 (s, 9H, N-Boc), 1.27 (s, 3H, 16-Me), 1.24 (s, 3H, 17-Me), 1.01-1.07 (m, 8H,); 13C (300 MHz, CDCl$_3$) d 205.4, 172.0, 171.6, 171.3, 170.0, 164.8, 156.1, 154.8, 139.7, 136.3, 134.0, 130.3, 128.9, 128.4, 115.5, 90.1, 84.6, 81.2, 81.0, 77.8, 76.7, 73.3, 71.9, 68.1, 58.3, 57.4, 51.2, 42.3, 39.1, 38.1, 35.7, 29.9, 29.1, 28.5, 25.0, 23.4, 23.3, 22.4, 21.2, 20.6, 16.4, 9.3.

EXAMPLE 36

13-Carbethoxy-7-TES-13,14-dehydro-baccatin

A solution of 13-keto-7-TES-baccatin (150 mg, 0.21 mmol) in anhydrous THF (5 mL) and DMPU (1 mL) under stirring is cooled to −70° C. under nitrogen. Potassium tert-butoxide (0.54 mL, 1M in THF, 0.54 mmol) is dropped therein and the mixture is kept under stirring at −65° C. for 45 minutes, then added with ClCOOEt (31 L, 0.31 mmol), checking the reaction by TLC: after 2 h 30 min, acetic acid (0.05 mL, 40% in THF) is dropped in the mixture, which is left to warm at room temperature. After dilution with a NaCl saturated solution (5 mL), the reaction mixture is extracted with AcOEt (2×5 mL) and the organic phase is washed with a NaCl saturated solution (5 mL), dried ($Na_2SO_4$) and evaporated. The residue is purified by chromatography on silica (1→5% AcOEt in $CH_2Cl_2$) to obtain the title product (136 mg, 82%).

$R_f$=0.55 (silica, 50% AcOEt in cyclohexane); $^1H$-NMR (200 MHz, $CDCl_3$) δ 8.09 (d, J=7.0 Hz, 2H, Bz), 7.45-7.62 (m, 3H, Bz,), 6.45 (s, 1H, 10-H), 5.83 (d, J=7.4 Hz, 1H, 2-H), 5.38 (s, 1H, 14-H), 4.98 (d, J=8.4 Hz, 1H, 5-H), 4.46 (dd, J=6.9, 3.7 Hz, 1H, 7-H), 4.16-4.35 (m, 4H, 20-H, $COOCH_2CH_3$,), 3.76 (d, J=5.5 Hz, 1H, 3-H), 2.47-2.62 (m, 1H, 6-H), 2.28 (s, 3H, 4-OAc), 2.20 (s, 3H, 10-OAc), 2.04 (s, 3H; 18-Me), 1.84-1.98 (m, 1H, 6-H), 1.72 (s, 3H, 19-Me), 1.46 (s, 3H, 16-Me), 1.37 (s, 3H, 17-Me), 1.33 (m, 3H, $COOCH_2CH_3$), 0.90-0.98 (t, J=8.7 Hz, 9H, $Si(CH_2CH_3)_3$), 0.57-0.65 (m, 6H, $Si(CH_2CH_3)_3$); $^{13}C$-NMR (300 MHz, $CDCl_3$) δ 201.5, 170.3, 169.3, 166.5, 153.0, 151.2, 136.9, 134.6, 133.7, 130.0, 129.3, 128.6, 119.1, 84.0, 80.6, 80.5, 75.3, 73.0, 72.2, 65.3, 58.3, 44.8, 41.0, 37.2, 27.6, 21.7, 21.0, 18.9, 14.2, 13.5, 10.0, 6.8, 5.3.

EXAMPLE 37

13-carbobenzyloxy-7-TES-13,14-dehydro-baccatin III

A solution of 13-keto-7-TES-baccatin III (150 mg, 0.21 mmol) in anhydrous THF (5 mL) and DMPU (1 mL) under stirring is cooled to −70°° C. under nitrogen. Potassium tert-butoxide (0.54 mL, 1M in THF, 0.54 mmol) is dropped in the mixture, which is kept under stirring at −65° C. for 45 minutes, then added with $ClCOOCH_2Ph$ (49 μL, 0.31 mmol), checking the reaction by TLC: after 2 h 30 min acetic acid (0.05 mL, 40% in THF) is dropped into the reaction, which is left to warm at room temperature. After dilution with a NaCl saturated solution (5 mL), the reaction mixture is extracted with AcOEt (2×5 mL) and the organic phase is washed with a NaCl saturated solution (5 mL), dried ($Na_2SO_4$) and evaporated. The residue is purified by chromatography on silica (1→3% AcOEt in $CH_2Cl_2$) to obtain the title product (117 mg, 67%).

$R_f$=0.6 (silica, 50% AcOEt in cyclohexane); $^1H$-NMR (200 MHz, $CDCl_3$) δ 8.09 (d, J=7.0 Hz, 2H, Bz), 7.37-7.62 (m, 8H, Bz, Ar,), 6.44 (s, 1H, 10-H), 5.83 (d, J=7.4 Hz, 1H, 2-H), 5.39 (s, 1H, 14-H), 5.25 (s, 2H, $CH_2$), 4.97 (d, J=8.0 Hz, 1H, 5-H), 4.45 (dd, J=7.0, 3.7 Hz, 1H, 7-H), 4.15-4.30 (Abq, 2H, 20-H), 3.74 (d, J=7.4 Hz, 1H, 3-H), 2.47-2.62 (m, 1H, 6-H), 2.25 (s, 3H, 4-OAc), 2.20 (s, 3H, 10-OAc), 2.01 (s, 3H; 18-Me), 1.84-1.98 (m, 1H, 6-H), 1.72 (s, 3H, 19-Me), 1.44 (s, 3H, 16-Me), 1.28 (s, 3H, 17-Me), 0.90-0.98 (t, J=8.7 Hz, 9H, $Si(CH_2CH_3)_3$), 0.57-0.65 (m, 6H, $Si(CH_2CH_3)_3$); $^{13}C$-NMR (300 MHz, $CDCl_3$) δ 201.5, 170.3, 169.3, 166.5, 153.0, 151.3, 137.0, 134.5, 133.7, 130.1, 129.3, 129.0, 128.8, 128.7, 128.6, 119.1, 84.0, 80.6, 80.5, 76.3, 75.3, 73.0, 72.2, 70.7, 58.3, 44.8, 41.0, 37.2, 27.7, 21.7, 21.0, 18.9, 13.5, 10.0, 6.8, 5.3.

EXAMPLE 38

14-hydroxy-13-keto-7-TES-baccatin III 1,14-sulfite

A solution of 14-hydroxy-13-keto-7-TES-baccatin (300 mg, 0.42 mmol) in Anhydrous $CH_2Cl_2$ (3 mL) is dropped into a solution of $SOCl_2$ (0.092 mL, 1.26 mmol) and triethylamine (0.35 mL, 2.52 mmol) in anhydrous $CH_2Cl_2$ (6 mL) at 0° C. The reaction mixture is kept under stirring for 20 minutes, then poured into ice-water (10 mL) and the separated organic phase is washed with water (10 mL), dried ($Na_2SO_4$) and evaporated. The residue is purified by silica chromatography (10→20% AcOEt in cyclohexane) to obtain the two sulfite isomers A (86 mg, 27%) and B (201 mg, 63%) as yellow solids.

Isomer A—$R_f$=0.65 (silica, 50% AcOEt in cyclohexane); $^1H$-NMR (200 MHz, $CDCl_3$) δ 8.09 (d, J=7.0 Hz, 2H, Bz), 7.44-7.65 (m, 3H, Bz), 6.59 (s, 1H, 10-H), 6.16 (d, J=6.2 Hz, 1H, 2-H), 5.16 (s, 1H, 14-H), 4.92 (d, J=8.4 Hz, 1H, 5-H), 4.50 (dd, J=6.6, 3.6 Hz, 1H, 7-H), 4.12-4.38 (Abq, 2H, 20-H), 3.99 (d, J=6.6 Hz, 1H, 3-H), 2.49-2.64 (m, 1H, 6-H), 2.25 (s, 3H, 4-OAc), 2.23 (s, 3H, 10-OAc), 2.19 (s, 3H; 18-Me), 1.84-1.98 (m, 1H, 6-H), 1.71 (s, 3H, 19-Me), 1.39 (s, 3H, 16-Me), 1.15 (s, 3H, 17-Me), 0.91-0.99 (t, J=8.7 Hz, 9H, $Si(CH_2CH_3)_3$), 0.58-0.66 (m, 6H, $Si(CH_2CH_3)_3$); MS: 760 M/Z.

Isomer B—$R_f$=0.60 (silica, 50% AcOEt in cyclohexane); $^1H$-NMR (200 MHz, $CDCl_3$) δ 8.03 (d, J=7.3 Hz, 2H, Bz), 7.49-7.68 (m, 3H, Bz), 6.55 (s, 1H, 10-H), 6.13 (d, J=6.9 Hz, 1H, 2-H), 4.92 (d, J=8.4 Hz, 1H, 5-H), 4.90 (s, 1H, 14-H), 4.50 (dd, J=6.3, 4.0 Hz, 1H, 7-H), 4.12-4.37 (Abq, 2H, 20-H), 3.91 (d, J=6.6 Hz, 1H, 3-H), 2.49-2.64 (m, 1H, 6-H), 2.26 (s, 3H, 4OAc), 2.25 (s, 3H, 10-OAc), 2.21 (s, 3H; 18-Me), 1.84-1.98 (m, 1H, 6-H), 1.75 (s, 3H, 19-Me), 1.35 (s, 6H, 16,17-Me), 0.91-0.99 (t, J=8.7 Hz, 9H, $Si(CH_2CH_3)_3$), 0.58-0.66 (m, 6H, $Si(CH_2CH_2)_3$); MS: 760 M/Z.

EXAMPLE 39

14-hydroxy-13-keto-7-TES-baccatin III 1,14-sulfate

Method A: a solution of 14-hydroxy-13-keto-7-TES-baccatin III (300 mg, 0.42 mmol) in anhydrous $CH_2Cl_2$ (3 mL) is dropped into a solution of $SO_2Cl_2$ (0.1 mL, 1.26 mmol) and triethylamine (0.35 mL, 2.52 mmol) in Anhydrous $CH_2Cl_2$ (6 mL) at 0° C. The reaction mixture is kept under stirring for 20 minutes, then poured into ice-water (10 mL) and the separated organic phase is washed with water (10 mL), dried ($Na_2SO_4$) and evaporated. The residue is purified by chromatography on silica (10→20% AcOEt in cyclohexane) to obtain the title product (145 mg, 45%) and a less polar product (53 mg) as yellow solids.

Method B: a solution of 14-hydroxy-13-keto-7-TES-baccatin III 1,14-sulfite (isomer B) (91 mg, 0.12 mmol) in $CCl_4$ (2 mL) and $CH_3CN$ (2 mL) is cooled to 0° C., then added in sequence with $RuCl_3$ (1 mg), $NaIO_4$ (38 mg, 0.18 mmol) and finally water (3 mL): the reaction mixture becomes dark and is stirred for 15 minutes, then poured into ethyl ether (10 mL)

and the two phases are separated. The aqueous phase is extracted with ethyl ether (5 mL) and the combined organic phases are dried (Na$_2$SO$_4$) and evaporated to obtain the title product (90 mg, 97%).

R$_f$=0.65 (silica, 50% AcOEt in cyclohexane); $^1$H-NMR (200 MHz, CDCl$_3$) δ 8.09 (d, J=7.0 Hz, 2H, Bz), 7.46-7.65 (m, 3H, Bz), 6.59 (s, 1H, 10-H), 6.18 (d, J=6.6 Hz, 1H, 2-H), 5.10 (s, 1H, 14-H), 4.92 (d, J=7.6 Hz, 1H, 5-H), 4.47 (dd, J=6.9, 3.7 Hz, 1H, 7-H), 4.08-4.38 (Abq, 2H, 20-H), 3.88 (d, J=6.6 Hz, 1H, 3-H), 2.49-2.64 (m, 1H, 6-H), 2.31 (s, 3H, 4-OAc), 2.27 (s, 3H, 10-OAc), 2.24 (s, 3H, 18-Me), 1.84-1.98 (m, 1H, 6-H), 1.70 (s, 3H, 19-Me), 1.44 (s, 3H, 16-Me), 1.36 (s, 3H, 17-Me), 0.91-0.99 (t, J=8.4 Hz, 9H, Si(CH$_2$CH$_3$)$_3$), 0.58-0.66 (m, 6H, Si(CH$_2$CH$_3$)$_3$).

EXAMPLE 40

14β-hydroxy-2-debenzoyl-2-m-methoxybenzoyl-7-TES-13-ketobaccatin III

A solution 1M in THF of t-BuOK (2.5 ml, 0.86 mmol) cooled to −50° C. is dropped into a solution of 2-debenzoyl-2-m-methoxybenzoyl-7-TES-13-ketobaccatin III (670 mg, 0.96 mmol) in anhydrous THF (9 ml) and DMPU (2 ml), cooled at −50° C. The solution is kept under stirring at −60° C. for 45 minutes, then added drop by drop with a solution of (±)-camphorsulfonyl-oxaziridine (440 mg, 2 mmol) in anhydrous THF (2 ml). The mixture is stirred for 3 hours at −60° C. then treated with a 10% glacial acetic acid solution in anhydrous THF (2 ml). The mixture is left to warm at room temperature, then extracted with DCM (2×10 ml). The combined organic phases are washed with water, brine, and dried over Na$_2$SO$_4$. The crude product is used for the subsequent step without further purification. $^1$H-NMR (200 MHz, CDCl$_3$) δ 0.58-0.66 (m, 6H, Si—CH$_2$); 0.91-0.99 (t, J=8.7, 9H, CH$_2$CH$_3$); 1.24 (s, 3H, 17-Me); 1.28 (s, 3H, 16-Me); 1.75 (s, 3H, 19-Me); 1.83-2.05 (m, 1H, 6-H); 2.14 (s, 3H, 18-Me); 2.24 (s, 3H, 10-OAc); 2.26 (s, 3H, 4-OAc); 2.46-2.61 (m, 1H, 6-H); 3.64 (s, 1H, 1-OH) 3.73 (d, J=1.8, 1H, 14-OH); 3.87 (d, J=6.9, 1H, 3-H); 4.14 (d, J=1.8, 1H, 14-H); 4.31 (s, 2H, 20-H); 4.49 (dd, J=10.7, 6.6, 1H, 7-H); 4.93 (d, J=7.3, 1H, 5-H); 5.89 (d, J=7.0, 1H, 2-H); 6.53 (s, 1H, 10-H); 7.54 (2', 1H, m), 7.13 (4', 1H, dd, 7.9, 3.0), 7.36 (5', 1H, t, 7.9 Hz), 7.61 (6', 1H, d 7.9), 3.85 (OMe, 3H, s).

EXAMPLE 41

14β-hydroxy-2-debenzoyl-2-m-methoxybenzoyl-7-TES-13-ketobaccatin III 1,14-carbonate A solution of 14β-hydroxy-2-debenzoyl-2-m-methoxybenzoyl-7-TES-13-ketobaccatin III (12.2 g) in anhydrous DCM (50 ml) and pyridine (16 ml) is dropped into a 20% phosgene solution in DCM (45 mL, 5 eq) at −10° C. After 2 hours, a 5% NaHCO$_3$ aqueous solution (100 ml) is dropped therein. The aqueous phase is back-extracted with DCM (3×50 ml). The combined organic phases are dried over sodium sulfate and evaporated. The reaction product crude is purified by flash chromatography (silica gel, DCM-AcOEt=50:1) to give the desired compound in 95% yield. $^1$H-NMR (200 MHz, CDCl$_3$) δ 0.58-0.66 (m, 6H, Si—CH$_2$); 0.91-0.99 (t, J=8.7, 9H, CH$_2$CH$_3$); 1.21 (s, 3H, 17-Me); 1.39 (s, 3H, 16-Me); 1.75 (s, 3H, 19-Me); 1.86-2.13 (m, 1H, 6-H); 2.22 (s, 3H, 18-Me); 2.25 (s, 3H, 10-OAc); 2.26 (s, 3H, 4-OAc); 2.48-2.63 (m, 1H, 6-H); 3.83 (d, J=7.0, 1H, 3-H); 4.30 (ABq, 2H, 20-H); 4.49 (d, J=11.0, 7.0, 1H, 7-H); 4.81 (s, 1H, 14-H); 4.93 (d, J=7.3, 1H, 5-H); 6.15 (d, J=7.0, 1H, 2-H); 6.54 (s, 1H, 10-H); 7.54 (2', 1H, m), 7.13 (4', 1H, dd, 7.9, 3.0), 7.36 (5', 1H, t, 7.9 Hz), 7.61 (6', 1H, d 7.9), 3.85 (OMe, 3H, s).

EXAMPLE 42

14β-hydroxy-2-debenzoyl-2-m-methoxybenzoyl-7-TES-baccatin III 1,14-carbonate

A suspension of tetraethylammonium borohydride (12 eq) in absolute methanol (10 ml) is cooled to −50° C. and added to a solution of 14β-hydroxy-2-debenzoyl-2-m-methoxybenzoyl-7-TES-13-ketobaccatin III 1,14-carbonate (0.5 g, 0.6 mmol) in methanol (10 ml). After disappearance of the starting material (8 h), the reaction is treated with citric acid, then extracted with ethyl acetate. The combined organic phases are dried over sodium sulfate and evaporated. The resulting crude is purified by chromatography to give the desired compound in a 60% yield. $^1$H-NMR (200 MHz, CDCl$_3$) δ 0.58-0.66 (m, 6H, Si—CH$_2$); 0.91-0.99 (t, J=8.7, 9H, CH$_2$CH$_3$); 1.16 (s, 3H, 17-Me); 1.28 (s, 3H, 16-Me); 1.74 (s, 3H, 19-Me); 1.85-2.14 (m, 1H, 6-H); 2.06 (s, 3H, 18-Me); 2.21 (s, 3H, 10-OAc); 2.33 (s, 3H, 4-OAc); 2.47-2.65 (m, 1H, 6-H); 3.74 (d, J=7.4, 1H, 3-H); 4.12-4.35 (m, 2H, 20-H); 4.49 (dd, J=10.3, 6.6, 1H, 7-H); 4.82 (d, 1H, 14-H); 4.99 (d, J=7.3, 1H, 5-H); 5.00-5.03 (m, 1H, 13-H); 6.11 (d, J=7.4, 1H, 2-H); 6.45 (s, 1H, 10-H); 7.54 (2', 1H, m), 7.13 (4', 1H, dd, 7.9, 3.0), 7.36 (5', 1H, t, 7.9 Hz), 7.61 (6', 1H, d 7.9), 3.85 (OMe, 3H, s).

EXAMPLE 43

13-[N-Boc-N,O-(2,4-dimethoxybenzylidene)-β-isobutylisoserinoyl]-14β-hydroxy-2-debenzoyl-2-m-methoxybenzoyl-7-TES-baccatin III 1,14-carbonate The product is obtained from 14β-hydroxy-2-debenzoyl-2-m-methoxybenzoyl-7-TES-baccatin III 1,14-carbonate following the same procedure as described in Example 33. $^1$H-NMR: (CDCl$_3$, 300 MHz) δ 6.17, (H2, d, 8.5 Hz), 3.78, (H3, d, 8.3 Hz), 4.95, (H5, dd, 9.5, 1.1 Hz), 2.54, (H6α, m), 1.90, (H6β, m), 3.96, (H7, d, 6.7 Hz), 6.51, (H10, s), 6.49, (H13, m), 4.87, (H14, d, 6.8 Hz), 1.40, (H16, s), 1.35, (H17, s), 2.18, (H18, s), 1.76, (H19, s), 4.29, (H20α, AB System, 22.6, 8.3 Hz), 6.51, (H2', m), 7.29, (H3', m), 1.65, (H4', m), 1.88, (H5', m), 1.12, (H6', d, 6.3 Hz), 1.12, (H7', d, 6.3 Hz), 2.34, (4Ac, s), 2.24, (10Ac, s), 1.40, (Boc, s), 8.06, 6.51, (2,4diMeOPhCH, m), 3.91, (MeO Ph, s), 3.86, (MeO Ph, s), 2.81, (OH, br s), 1.56, (OH, br s), 0.97, (CH$_3$Tes, t, 8.1), 0.62, (CH$_2$Tes, q, 8.1 Hz), 7.54 (2', 1H, m), 7.13 (4', 1H, dd, 7.9, 3.0), 7.36 (5', 1H, t, 7.9 Hz), 7.61 (6', 1H, d 7.9), 3.85 (OMe, 3H, s).

EXAMPLE 44

13-[N-Boc-N,O-(2,4-dimethoxybenzylidene)-β-isobutylisoserinoyl]-14β-hydroxy-2-debenzoyl-2-m-methoxybenzoylbaccatin III 1,14-carbonate The product is obtained from 13-[N-Boc-N,O-(2,4-dimethoxybenzylidene)-β-isobutylisoserinoyl]-14β-hydroxy-2-debenzoyl-2-m-methoxybenzoyl-7-TES-baccatin III 1,14-carbonate following the same procedure as described in Example 34. $^1$H-NMR: (CDCl$_3$, 300 MHz) δ 6.16 (H2, d 7.5 Hz), 3.78 (H3, d 7.4 Hz), 4.98 (H5, dd 9.5, 2.2 Hz), 2.59 (H6α, ddd 15.0, 9.8, 6.4 Hz), 1.94 (H6β, ddd 14.9, 11.4, 2.7 Hz), 4.48 (H7, dd 10.9, 6.5 Hz), 6.34 (H10, s), 6.52 (H13, m), 4.87 (H14, d 6.7 Hz), 1.40 (H16, s), 1.33 (H17, s), 2.05 (H18, s), 1.76 (H19, s), 4.33 (H20α, d 8.3), 4.27 (H20β, d 8.3 Hz), 6.53 (H2', m), 7.29 (H3', m), 1.65-1.88 (H4', m), 1.77 (H5', m), 1.11 (H6', d 6.2 Hz), 1.11 (H7', d 6.2 Hz), 2.30(4Ac, s), 2.34(10Ac, s), 1.40 (Boc, s), 6.51-6.57(2,4 diMeOPhCH, m), 3.91 (MeO Ph, s), 3.86 (MeO Ph, s), 2.81 (OH, br s) 7.54 (2', 1H, m), 7.13 (4', 1H, dd, 7.9, 3.0), 7.36 (5', 1H, t, 7.9 Hz), 7.61 (6', 1H, d 7.9), 3.85 (OMe, 3H, s).

EXAMPLE 45

13-(N-Boc-β-isobutylisoserinoyl)-14β-hydroxy-2-debenzoyl-2-m-methoxybenzoylbaccatin III 1,14-carbonate The product is obtained from 13-[N-Boc-N,O-(2,4-dimethoxybenzylidene)-β-isobutylisoserinoyl]-14β-hydroxy-2-debenzoyl-2-m-methoxybenzoyl-7-TES-baccatin III 1,14-carbonate following the same procedure as described in Example 35. $^1$H-NMR (200 MHz, CDCl$_3$) δ 6.09 (2, 1H, d, 7.3 Hz), 3.68 (3, 1H, d, 7.4 Hz), 4.93 (5, 1H, dd, 9.7, 2.5 Hz), 2.52 (6α, 1H, ddd, 14.8, 9.8, 6.9 Hz), 1.86 (6β, 1H, m), 4.37 (7, 1H, m), 6.25 (10, 1H, s), 6.44 (13, 1H, d, broad, 6.9 Hz), 4.83 (14, 1H, d, 6.9 Hz), 1.26 (16, 3H, s), 1.33 (17, 3H, s), 1.88 (18, 3H, d, 1.6 Hz), 1.70 (19, 3H, s), 4.32 (20a, 1H, d, 8.3 Hz), 4.20 (20b, 1H, d, 8.3 Hz), 2.46 (4-CO$_2$CH$_3$, 3H, s), 2.23 (10-CO$_2$CH$_3$, 3H, s), 4.30 (2', 1H, dd, 6.4, 3.2 Hz), 4.08 (3', 1H, m), 1.21 (4'a, 1H, m), 1.43 (4'b, 1H, m), 1.68 (5', 1H, m), 0.96 (6'a, 3H, d, 6.3 Hz), 0.95 (6'b, 3H, d, 6.3 Hz), 1.34 (Boc, 9H, s), 4.73 (NH, 1H, d, 9.8. Hz), 7.54 (2", 1H, m), 7.13 (4", 1H, dd, 7.9, 3.0), 7.36 (5", 1H, t, 7.9 Hz), 7.61 (6", 1H, d 7.9), 3.85 (OMe, 3H, s).

The invention claimed is:

1. A compound of formula III

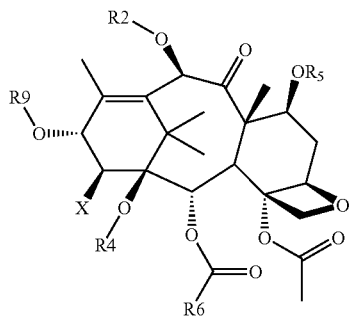

wherein

X is selected from the group consisting of —N$_3$, —NH$_2$, —NH—R$_3$ and =CH—R$_8$;

R$_2$ is hydrogen or acyl;

R$_3$ is C$_1$-C$_4$ alkoxycarbonyl or, taken together with R$_4$, forms a carbonyl, thiocarbonyl, SO, SO$_2$ group;

R$_4$ is hydrogen or, taken together with R$_3$ or R$_8$, forms the groups specified in the respective definitions of R$_3$ and R$_8$;

R$_5$ is hydrogen or an alcohol-protecting group;

R$_6$ is aryl, substituted aryl, heteroaryl;

R$_8$ is hydrogen, C$_1$-C$_4$ alkyl, C$_1$-C$_4$ alkoxycarbonyl or, taken together with R$_4$, forms a carbonyl group;

R$_9$ is an acyl or hydroxyaminoacyl group.

2. A process for the preparation of a compound of formula III from a compound of formula II

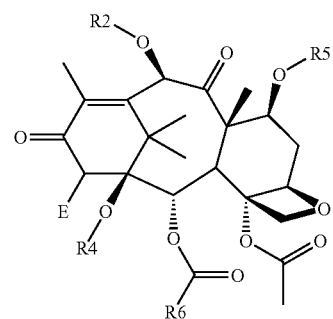

wherein

E is selected from the group consisting of —N$_3$, —NH—R$_3$ and =CH—R$_8$ and R$_2$, R$_5$, R$_4$ and R$_6$ are as defined according to claim 1, which process comprises:

a) reduction of the C13 carbonyl to give compounds of formula VII

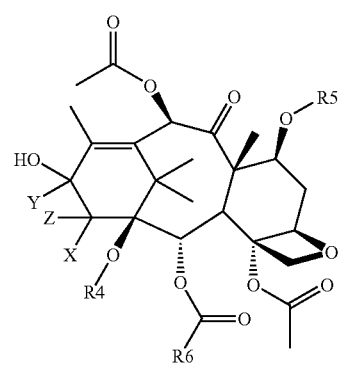

wherein

X is —N$_3$, —NH—R$_3$, —CH$_2$—R$_8$;

Y and Z are hydrogen or, when X is —CH$_2$—R$_8$, are taken together to form a double bond;

and the other groups are defined as above;

b) esterification at the 13-position with derivatives of acids of formula IX to give compounds of formula VIII

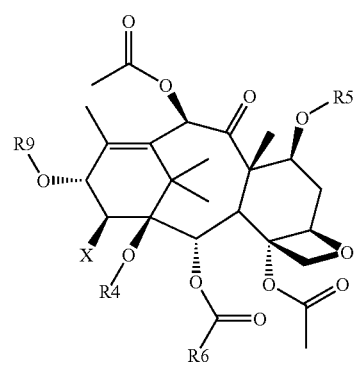

wherein
$R_4$, $R_5$, $R_6$, $R_9$ and X are as defined above;
c) optional cleavage of the protective groups.

3. A process for the preparation of a compound of formula II from a compound of formula I,

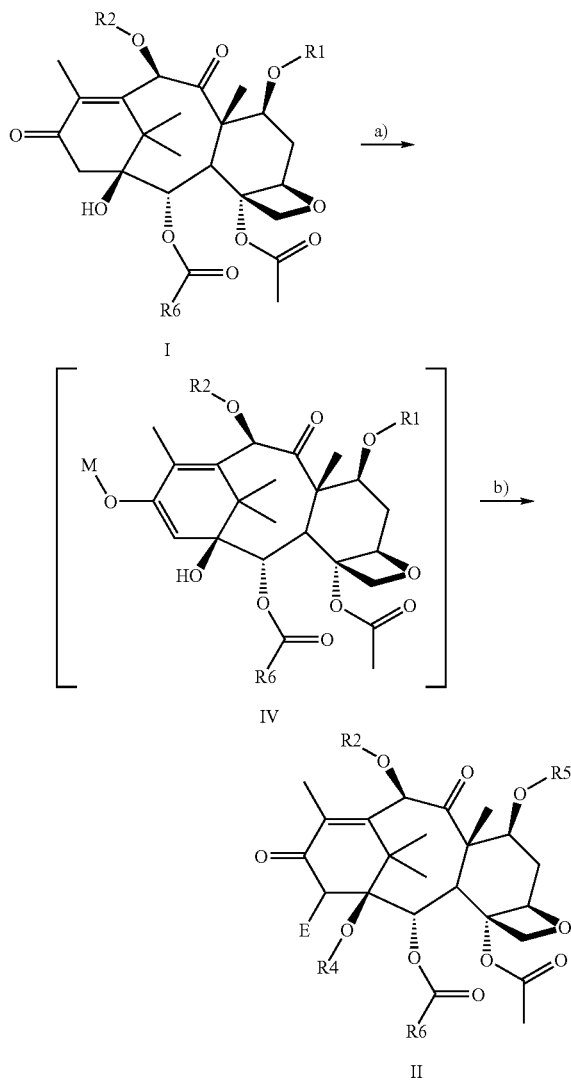

wherein $R_1$ is an alcohol-protecting group;
$R_2$ is an acyl group or an alcohol-protecting group;
E is =$N_2$, —$N_3$, —$NH_2$2, —NH—$R_3$, —NH—$NH_2$, —NH—N=N—Ts, —NH—N=N—Boc, —N($CO_2R_7$)NHCO$_2R_7$, =CH—$R_8$;
Ts is p-toluenesulfonyl;
$R_3$ is $C_1$-$C_4$ alkoxycarbonyl or, taken together with $R_4$, forms a carbonyl, thiocarbonyl, SO, $SO_2$ group;
$R_4$ is hydrogen or, taken together with $R_3$ or $R_8$, forms the groups specified in the respective definitions of $R_3$ and $R_8$;
$R_5$ is hydrogen or an alcohol-protecting group;
$R_6$ is aryl, substituted aryl, heteroaryl;
$R_7$ is a $C_1$-$C_4$ alkyl, aryl or arylalkyl group,
$R_8$ is hydrogen, $C_1$-$C_4$ alkyl, $C_1$-$C_4$ alkoxycarbonyl or, taken together with $R_4$, forms a carbonyl group, which process comprises:

a) treating the 7-protected 13-ketobaccatin of formula I with bases to form an enolate intermediate of formula IV;
b) quenching the enolate IV with a suitable electrophile which can be converted to an E group or with an acylating, alkylating or silylating agent to give compounds of formula V

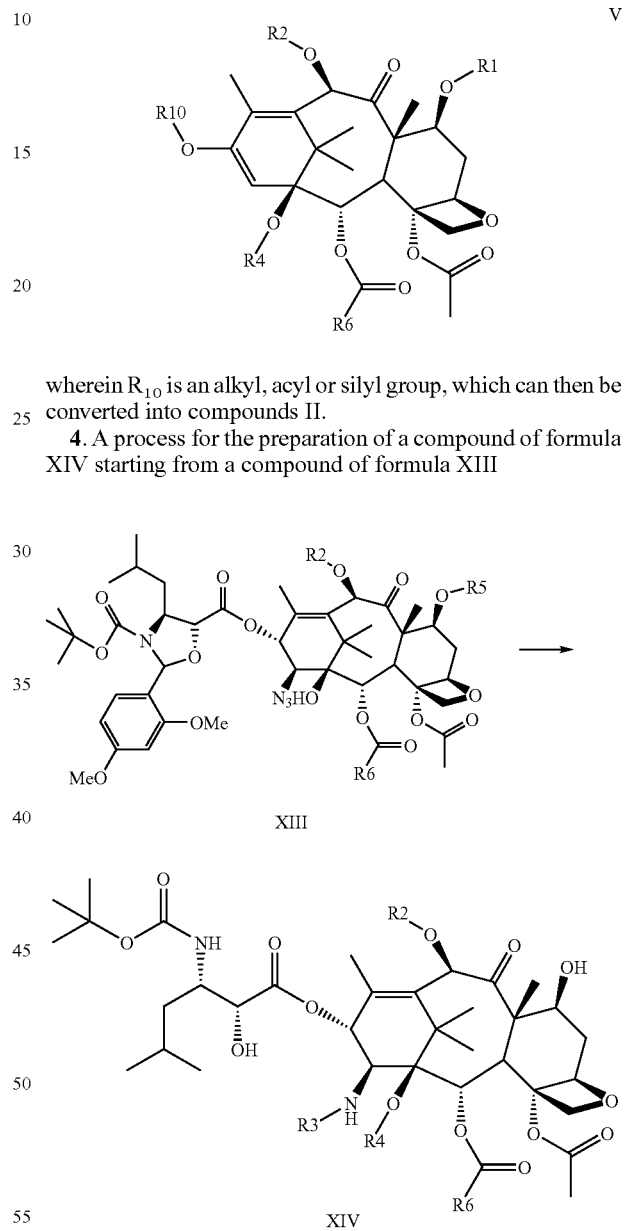

wherein $R_{10}$ is an alkyl, acyl or silyl group, which can then be converted into compounds II.

4. A process for the preparation of a compound of formula XIV starting from a compound of formula XIII wherein
$R_2$ is an acyl group or an alcohol-protecting group;
$R_3$ is hydrogen, acyl, alkyl or, taken together with $R_4$, forms a C=O, C=S, SO, $SO_2$ group;
$R_4$ is hydrogen or, taken together with $R_3$, forms a C=O, C=S, SO, $SO_2$ group;
$R_5$ is hydrogen or an alcohol-protecting group;
$R_6$ is aryl, substituted aryl, heteroaryl; comprising:
a) selective reduction of the azido group to amino group;
b) optional treatment with alkylating or acylating agents;

c) cleavage of the C7 protective group;
d) opening of the oxazolidine.

5. A compound of formula II

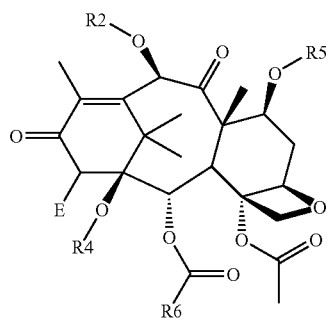

wherein
- $R_2$ is an acyl group or an alcohol-protecting group;
- E is $=N_2$, $-N_3$, $-NH_2$, $-NH-R_3$, $-NH-NH_2$, $-NH-N=N-Ts$, $-NH-N=N-Boc$, $-N(CO_2R_7)NHCO_2R_7$, $=CH-R_8$;
- $R_4$ is hydrogen;
- $R_5$ is hydrogen or an alcohol-protecting group;
- $R_6$ is aryl, substituted aryl, heteroaryl.

6. A compound of formula IV or V

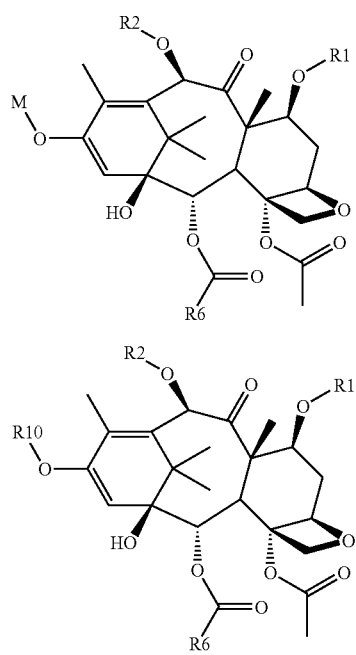

wherein
- M is an alkali metal;
- $R_{10}$ is an acyl, alkyl, silyl or phospho group;
- wherein $R_1$ is an alcohol-protecting group;
- $R_2$ is an acyl group or an alcohol-protecting group; and
- $R_6$ is aryl, substituted aryl, heteroaryl.

7. A compound of formula VII

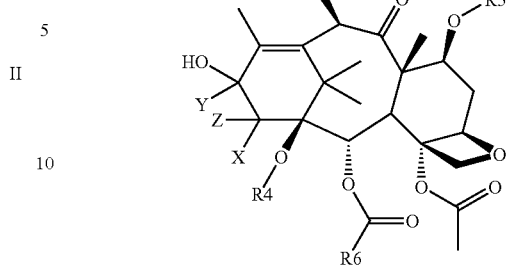

wherein
- $R_2$ is hydrogen or acyl;
- $R_4$ is hydrogen;
- $R_5$ is hydrogen or an alcohol-protecting group;
- $R_6$ is aryl, substituted aryl, heteroaryl;
- X is $-N_3$, $-NH-R_3$, $-CH_2-R_8$; and
- Y and Z are hydrogen or, when X is $-CH_2-R_8$, are taken together to form a double bond.

8. A compound of formula XI or XII

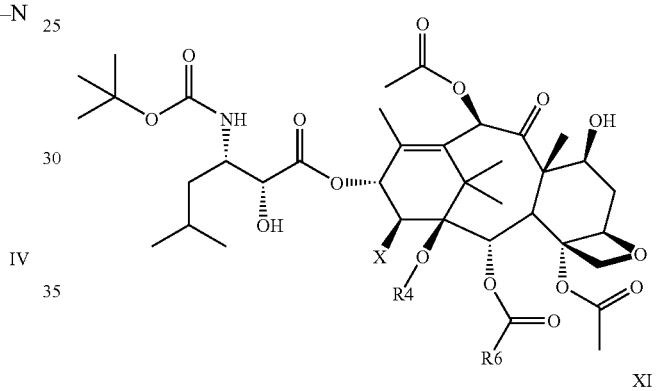

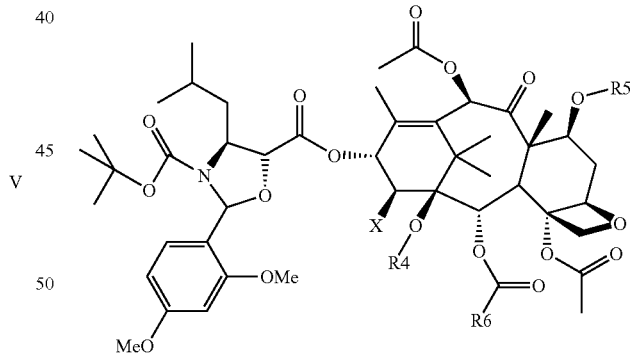

wherein
- X is selected from the group consisting of $-N_3$, $-NH-R_3$ and $=CH-R_8$;
- $R_3$ is an alkoxycarbonyl or, taken together with $R_4$, forms a carbonyl, thiocarbonyl, SO, $SO_2$ group;
- $R_4$ is hydrogen or, taken together with $R_3$ or $R_8$, forms the groups specified in the respective definitions of $R_3$ and $R_8$;
- $R_6$ is aryl, substituted aryl or heteroaryl;
- $R_5$ is hydrogen or an alcohol-protecting group;
- $R_8$ is hydrogen, $C_1$-$C_4$ alkyl, $C_1$-$C_4$ alkoxycarbonyl or, taken together with $R_4$, forms a carbonyl group.

* * * * *